United States Patent
Simpson et al.

(10) Patent No.: US 6,949,694 B2
(45) Date of Patent: Sep. 27, 2005

(54) METHODS AND MEANS FOR MODIFICATION OF PLANT CHARACTERISTICS

(75) Inventors: Gordon Grant Simpson, Norwich (GB); Caroline Dean, Norwich (GB); Paul Dijkwel, Borger (NL)

(73) Assignee: Pioneer Hi-Bred International, Inc., Johnston, IA (US)

( * ) Notice: Subject to any disclaimer, the term of this patent is extended or adjusted under 35 U.S.C. 154(b) by 321 days.

(21) Appl. No.: 10/192,985

(22) Filed: Jul. 11, 2002

(65) Prior Publication Data

US 2003/0084483 A1 May 1, 2003

(30) Foreign Application Priority Data

Jul. 12, 2001 (GB) .............................................. 0117054

(51) Int. Cl.⁷ ........................ C12N 15/29; C12N 15/82; C12N 5/10; C12N 5/04; A01H 5/00
(52) U.S. Cl. ....................... 800/290; 800/278; 800/298; 800/287; 800/320.1; 536/23.6; 536/24.1; 435/320.1; 435/410; 435/419; 435/468
(58) Field of Search .............................. 800/320.1, 278, 800/290, 298, 287; 536/23.6, 24.1, 23.1; 435/320.1, 410, 419, 468

(56) References Cited

PUBLICATIONS

MacDonald et al (2003, Cell 113:671–672).*
Simpson et al (2003, Cell 113:777–787).*
Larkin et al (1994, The Plant Cell 6:1065–1076).*
Bevan, M. et al.; Untitled Journal submitted (Aug. 28, 2000) MIPS at the Max–Planck–Institut fuer Biochemie, Am Klopferspitz 18a, D–83152 Martinsried, FRG; Gen Bank Accession No.: AL391710.
Reid, S.P. et al. "An EST database from Sorghum: developing embryos"; (unpublished–2000); Gen Bank Accession No.: BG411183.
Reid, S.P. et al. "An EST database from Sorghum: developing embryos"; (unpublished–2000); Gen Bank Accession No.: BG487457.
Shoemaker, R. et al. "Public Soybean EST Project", (unpublished–1999); Gen Bank Accession No.: BE020144.
Alcala, J. et al. "Generation of ESTs from tomato callus tissue"; (unpublished–1999); Gen Bank Accession No.: AW035163.
Van Der Hoeven, R. et al. "Generation of ESTs from potato swelling stolons"; (unpublished–1999); Gen Bank Accession No.: BE471952.
White, J.A. et al. "A new set of Arabidopsis expressed sequence tags from developing seeds. The metabolic pathway from carbohydrates to seed oil"; Plant Physiol., 124(4): 1582–1594 (2000); Gen Bank Accession No.: BG459222.

* cited by examiner

*Primary Examiner*—David T. Fox
*Assistant Examiner*—Stuart F. Baum
(74) *Attorney, Agent, or Firm*—Dann, Dorfman, Herrell and Skillman; Kathleen D. Rigaut

(57) ABSTRACT

The invention discloses nucleic acid encoding an FY polypeptide with the sequence shown in Annex 2. Also provided are vectors, host cells and plants. Methods of the invention include the use of nucleic acids to express or down-regulate FY in plants. The methods may be used to affect flowering time or juvenile phase length in plants.

16 Claims, No Drawings

SEQUENCE LISTING

<160> NUMBER OF SEQ ID NOS: 31

<210> SEQ ID NO 1
<211> LENGTH: 643
<212> TYPE: PRT
<213> ORGANISM: Arabidopsis thaliana

<400> SEQUENCE: 1

Met Tyr Ala Gly Gly Asp Met His Arg Gly Ser Gln Met Pro Gln Pro
  1               5                  10                  15

Pro Met Met Arg Gln Ser Ser Ala Ser Ser Thr Asn Ile Asn Pro Asp
                 20                  25                  30

Tyr His His Pro Ser Gly Pro Phe Asp Pro Asn Val Asp Ser Phe Gly
             35                  40                  45

Ala Lys Arg Met Arg Lys His Thr Gln Arg Arg Ala Val Asp Tyr Thr
         50                  55                  60

Ser Thr Val Val Arg Tyr Ile Gln Ala Arg Thr Trp Gln Arg Asp Ser
 65                  70                  75                  80

Arg Asp Arg Thr Thr Leu Gln Pro Thr Pro Ala Ala Ala Val Asp Met
                 85                  90                  95

Leu Pro Thr Val Ala Tyr Ser Asp Asn Pro Ser Thr Ser Phe Ala Ala
            100                 105                 110

```
Lys Phe Val His Ala Ser Leu Asn Lys Asn Arg Cys Ser Ile Asn Arg
            115                 120                 125

Val Leu Trp Thr Pro Ser Gly Arg Arg Leu Ile Thr Gly Ser Gln Ser
        130                 135                 140

Gly Glu Phe Thr Leu Trp Asn Gly Gln Ser Phe Asn Phe Glu Met Ile
145                 150                 155                 160

Leu Gln Ala His Asp Gln Pro Ile Arg Ser Met Val Trp Ser His Asn
                165                 170                 175

Glu Asn Tyr Met Val Ser Gly Asp Asp Gly Thr Leu Lys Tyr Trp
            180                 185                 190

Gln Asn Asn Met Asn Asn Val Lys Ala Asn Lys Thr Ala His Lys Glu
        195                 200                 205

Ser Ile Arg Asp Leu Ser Phe Cys Lys Thr Asp Leu Lys Phe Cys Ser
        210                 215                 220

Cys Ser Asp Asp Thr Thr Val Lys Val Trp Asp Phe Thr Lys Cys Val
225                 230                 235                 240

Asp Glu Ser Ser Leu Thr Gly Ala Gly His Gly Trp Asp Val Lys Ser
                245                 250                 255

Val Asp Trp His Pro Thr Lys Ser Leu Leu Val Ser Gly Gly Lys Asp
            260                 265                 270

Gln Leu Val Lys Leu Trp Asp Thr Arg Ser Gly Arg Glu Leu Cys Ser
        275                 280                 285

Leu His Gly His Lys Asn Ile Val Leu Ser Val Lys Trp Asn Gln Asn
        290                 295                 300

Gly Asn Trp Leu Leu Thr Ala Ser Lys Asp Gln Ile Ile Lys His Leu
305                 310                 315                 320

Tyr Asp Thr Tyr Ala Cys Asn Leu Gln Leu Tyr Asp Ile Arg Thr Met
                325                 330                 335

Lys Glu Leu Gln Ser Phe Arg Gly His Thr Lys Asp Leu Trp Arg Gly
            340                 345                 350

Ile Pro Ala Met Lys Asn Ile Leu Ser Val Gly Ala Leu Thr Ala Pro
        355                 360                 365

Phe Val Ile Gly Leu Trp Gly Arg His Glu Asn Pro Gln Ile Glu Ile
370                 375                 380

Pro Asn Ala His Asp Asn Val Trp Asp Leu Ala Trp His Pro Ile Gly
385                 390                 395                 400

Tyr Leu Leu Cys Arg Pro Ala Asp Asn Pro Arg Asp Val Leu Met Gln
                405                 410                 415

Asn Gln Gly Tyr Asn Glu Gln Gly Phe Gly Arg Gln Pro Asp Asn Phe
            420                 425                 430

Gln Pro Ser Glu Ala Ser Pro Ile Pro Gly Ala Phe Val Pro Gly Leu
        435                 440                 445

Thr Arg Asn Glu Gly Thr Ile Pro Gly Ile Gly Ile Ala Met Pro Phe
        450                 455                 460

Asp Ala Ser Ser Gln Gly Asp His Lys Gln Pro Leu Pro Gly Ser Met
465                 470                 475                 480

Ala Leu Gly Ala Pro Pro Leu Pro Pro Gly Pro His Pro Ser Leu Leu
                485                 490                 495

Gly Ser Gly Gln Gln Gln Gly Tyr Gln Gln Gln Gln His Gln Gly
            500                 505                 510

His Pro Gln Gln Met Leu Pro Met Pro Asn Met Pro His His Gln Leu
        515                 520                 525
```

```
Pro Pro Ser Ser His Met Pro Leu His Pro His His Leu Pro Arg Pro
        530                 535                 540

Met Gln Met Pro Pro His Gly His Met Pro Pro Ser Met Pro Met
545                 550                 555                 560

Ser His Gln Met Pro Gly Ser Met Gly Met Gln Gly Gly Met Asn Pro
                565                 570                 575

Gln Met Ser Gln Ser His Phe Met Gly Ala Pro Ser Gly Val Phe Gln
            580                 585                 590

Gly Gln Pro Asn Ser Gly Gly Pro Gln Met Tyr Pro Gln Gly Arg Gly
            595                 600                 605

Gly Phe Asn Arg Pro Gln Met Ile Pro Gly Tyr Asn Asn Pro Phe Gln
    610                 615                 620

Gln Gln Gln Pro Pro Leu Pro Pro Gly Pro Pro Asn Asn Asn Gln
625                 630                 635                 640

Gln His Gln

<210> SEQ ID NO 2
<211> LENGTH: 4920
<212> TYPE: DNA
<213> ORGANISM: Arabidopsis thaliana

<400> SEQUENCE: 2
```

| | | | | | |
|---|---|---|---|---|---|
| ctactgatgt | tgctgattgt | tgtttggtgg | agggccagga | ggtaaaggtg | gctgctgctg | 60 |
| ctgcacgaaa | taaaatatag | acaacggatt | agtcaacgga | ttatgctatt | ttagctctac | 120 |
| attttcaaca | tctaatcata | ccattgaacc | tagctagtga | gtttaaaact | agctgagaaa | 180 |
| gttgtattgt | ggttcaatcg | tatcaggtgt | tttgcattgt | tgtgtagaca | ttttgcctat | 240 |
| ttgcacatat | atacatgtga | aacctttacg | ggtatactaa | ataacaaaag | actagtgttt | 300 |
| aaatgggacc | tgttggaaag | ggttgttgta | gcctggaatc | atctgtggac | ggttgaaacc | 360 |
| accacgtcct | tggggataca | tttggggtcc | gccactgttt | ggttgtcctt | gaaatactcc | 420 |
| tgaaggagca | cccataaaat | gactttgcga | catctgagga | ttcatgccac | cttgcattcc | 480 |
| ctactccaac | aacaagtgag | gattaatatc | tctttctaca | cctctctaag | atatcactaa | 540 |
| gaaaataaaa | caaagaggaa | tccaacacat | ggggtaccga | caaaagccag | gcttaagttg | 600 |
| tggttgaatt | acaagagatc | tgagggccat | accattgatc | caggcatctg | atgagacata | 660 |
| ggcattgagg | gaggtggcat | gtgaccgtga | ggaggcattt | gcataggccg | gggaagatga | 720 |
| tgagggtgca | atggcatatg | agatgatggt | ggtagctgat | ggtgaggcat | attgggcatt | 780 |
| ggaagcattt | gctggggatg | accttggtgt | tgttgttgtt | gctgataccc | ttgctgctgg | 840 |
| ccacttccaa | gaagcgatgg | gtggggacca | ggtggcaaag | gaggagcccc | cagtgccatg | 900 |
| gaacctggaa | gaggctgttt | atgatcccct | tgagaggatg | catcaaatgg | cattgctatt | 960 |
| cctattcctg | ggatagtccc | ctcgttccgt | gtcaacccag | gcacaaatgc | tccagggatt | 1020 |
| ggcgatgcct | cagatggttg | gaaattatca | ggttggcgac | caaaaccttg | ttcattatag | 1080 |
| cctgatacaa | attacgctta | tcagtacaca | caaatcacat | cttcaatttg | ttagtaaaca | 1140 |
| ctaaataaaa | aacactaatt | tctgacaaat | gcaacttgaa | agtacatgct | caaaattaaa | 1200 |
| acagtaagtg | agatactaat | gaccgagtac | ttgggtctga | gtttttaaag | cctgtagaaa | 1260 |
| tctgcaccta | tatcagatca | gctcagcttg | accagtcaag | tctgttcttt | tctacaaaaa | 1320 |
| aattcagtta | atcacggtgc | catatggctg | gccgagcctg | aaccttaaaa | agccaaggtc | 1380 |
| catttcgaac | cagccattat | aggagtatat | gactgaccct | gccagggcct | gaccagttaa | 1440 |

-continued

```
gcctatcaca acatccttac tactgagatg gataaggaca tagtaattat gtactaccca      1500
caacctatcc atcccaatgc ctactaaaaa atcagatact aatagcccaa aaacaaacct      1560
tggttctgca taagaacatc tcggggatta tctgcaggcc tgtttctgca ccaaaacttg      1620
gttgtgtgat cattgctacc actgcagata taggggttaa aaatcattat ctgaagcatt      1680
tagttattca agagcacagg gaaccacaac acatcataga ataaaactgt aaggaactca      1740
tagcaccaga ctattgaaat tgctacctgc aaagaagata tccaatagga tgccatgcaa      1800
gatcccaaac actgttatca tgagcatttg ggatttcaat ctgcgggttt tcatgcctgg      1860
gaattaagaa aagttttcat aattagatac acctcaaaca aaaaccacaa aatataaggt      1920
aaagtaagat gctactagac tactagtatg tagatgcatc atgactgaat ataaaatgta      1980
gagaagaaac atgatttaaa aaacccttat aagtgattaa aacaatagca gcatgaacga      2040
ataaataaaa cagcatactg ctgcacaaca gtacctaccc cacaatccaa tgacaaatgg      2100
agccgtcaga gctcccactg acaaaatatt cttcatggca gggatgccac gccaaagctt      2160
aaaaagagtt aagacaactt ttaattagaa atagttgcaa attagaaata tcgaagaaac      2220
aaattgaaaa ctcgcatcca tgggataatg tctcatatgt cgacaagtaa agcatgggta      2280
caatgataat cttcaaagg catatactct agagtcctag tcaatgtaca gaaaagtaat       2340
ttgatgcggc cagtttgtct gatttcacgt gtttaaaaca tgatcattat agaatttgac      2400
agcttacatg ttacatcttt cgtgtgccca cgaaaggatt gaagctcctt catagtcctt      2460
atatcataca gctgcagatt acatgcataa gtgtcataca aatgcttcca taatgcaagg      2520
aaaaaatctc atttacaaat caatatcccc cccccccccc cccacccaaa agaaagtgag      2580
acttaccttta attatctgat cttttcgaggc cgttaaaagc caattgccat tttggttcca      2640
cttcacgcta agtactatgt ttttgtgacc atggctgcag aagtaagaat aggccatcaa      2700
attcgtcaaa gctttgaaca tgaaactata ataaaattac atattacatt atgtactact      2760
tacagtgagc aaagctctct cccagatcta gtatcccaga gtttgacaag ttggtctttt      2820
ccacctgaca acacagatta aagcggttaa tgatcagcca tagagaagct ctgaaatata      2880
cagcggtttc tttttattgc attattcaaa tagaagtcta taaaataatg taccagaaac      2940
tagtagggac tttgtggggt gccagtcaac gctcttgaca tcccaaccat ggcctgcctg      3000
agttcaaaat ataagaacc cttttgattac ttcgaaagtt ctcaaatatt acaaatatga      3060
agaaaactgt gaaacatgc ctccaaaagg ataggaaact tgttataagc accaatttgg      3120
aacctttaaa actaactaac gttacatggc atgacaccaa agcgaatctc aatgacacct      3180
tttcctatgt agcctaagaa tccaattcta ataacgtaca gcacatctca agcggccttc      3240
taaattcaaa ttagaagagc aagcaacaaa gaaataaagt atctgccgcc aatctgttca      3300
aataacatta ccggttaatg agctttcatc tacgcacttg gtaaaatccc agactttaac      3360
agtcgtatca tcagaacacg aacagaactt caaatctgtt ttacaaaaac tgttggatac      3420
acattgttca gttttgagag attcatttaa tgcaattcaa catatcaaac ttttttttac      3480
cttaaatcgc gaattgattc cttgtgagca gtttttattgg ctttcacatt gttcatattg      3540
ttctgccaat acctgataca taagaaacaa ttgatcctta ttgtcacagc atttgaatca      3600
tagaattctg agcttctcgt ttacaacatc ataagttagg gactgaaagg gaaaaacaaa      3660
tttactttaa tgtgcctcca tcatcaccag aaaccatata attttcattg tggctccata      3720
ccatcgacct aataggttga tcatgtgcct gatattgaca acaaatttaa acagtcaata      3780
ccaggagcag caactataga agaatcaaaa cagaagtttc aacagattag ttatacaatc      3840
```

-continued

```
tgagaaacga acctgaagaa tcatttcaaa attaaaagat tgcccattcc aaagagtaaa      3900
ctccccactt tgggagcccg tgataagacg tcttcctgaa ggtgtccact aaataaaaga      3960
aacccaatca gcaatgatcc cattaagttg gcataataga gttaaaacaa agaaagaaag      4020
atgttgcttt cttgaataga taaacatggc aaacagagaa taatacaaaa cacacagctg      4080
gtagagggat ataccaatac acggttgatt gaacaacggt tcttgtttag agatgcgtga      4140
acaaactttg cagcaaagct tgttgaagga ttatccgaat aggcaactgt gggaagcatc      4200
tgaagcattg atataaaagt tagatcagta aaccattcaa tcttattgca aaacccagaa      4260
aagcaaagaa atctaacatc aactgctgca gctggggttg gttgcagagt ggtcctatcc      4320
cttgagtctc gctgccatgt tcgagcctga acaaaaacat atatggagta aacactctct      4380
acttttagtt ccatataaag tatgagttcg ttgaactaca tatccatatc agttccatga      4440
cataaagaca atcctatcta atggcttttg agataaaaag gaccgaagaa ttcaactggg      4500
gaaagcagag gctatgagta tatagaccaa gactaaaact ttacagaaaa caagagaaat      4560
ataatcaagc agtacaaaag gttctaacaa agaaatactg tgagcagcaa tgggaataca      4620
ttacctgaat atatctaaca acggtgctgg tgtaatcaac agctcttctc tgtgtatgct      4680
ttctcattcg tttcgcccca aaactgtcta cattggctgc aacatcagac agagagacat      4740
taaatctcac agtcatcact aatccgataa aaggaagacg ctcaaagtct acttacggtc      4800 gaagggcca gatgggtggt ggtagtcggg attgatgtta gtggaagaag ctgacgactg       4860
ccgcatcatc ggtggttgtg gcatctgtga accctgtgc atatcgccgc cggcgtacat       4920
```

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Motif

<400> SEQUENCE: 3

Pro Pro Leu Pro
 1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Motif

<400> SEQUENCE: 4

Pro Pro Tyr Pro
 1

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Oligo

<400> SEQUENCE: 5
cctattaggt cgatggtatg g                                                21

<210> SEQ ID NO 6
<211> LENGTH: 21
<212> TYPE: DNA

```
<213> ORGANISM: Artificial Sequence
<220> FEATURE:
<223> OTHER INFORMATION: Description of Artificial Sequence: Oligo

<400> SEQUENCE: 6
acatggcatg acaccaaagc g                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Oligo

<400> SEQUENCE: 7
caacaatgta cgccggcggc g                                              21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Oligo

<400> SEQUENCE: 8
tggggttggt tgcagagtgg                                                20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Oligo

<400> SEQUENCE: 9
atcgcttctt ggaagtggcc                                                20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Oligo

<400> SEQUENCE: 10
tggacggttg aaaccaccac g                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Oligo

<400> SEQUENCE: 11
cttaactggt caggccctgg c                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Oligo

<400> SEQUENCE: 12
cattggaagc atttgctggg g                                              21
```

-continued

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Oligo

<400> SEQUENCE: 13
aaacccgcag attgaaatcc c                                          21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Oligo

<400> SEQUENCE: 14
aggtccattt cgaaccagcc                                            20

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Oligo

<400> SEQUENCE: 15
catagtactt agcgtgaagt gg                                         22

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Oligo

<400> SEQUENCE: 16
caatctgcgg gttttcatgc c                                          21

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Oligo

<400> SEQUENCE: 17
aattggattc ttaggctaca tagg                                       24

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Oligo

<400> SEQUENCE: 18
ctttcgaggc cgttaaaagc c                                          21

<210> SEQ ID NO 19
<211> LENGTH: 26
<212> TYPE: DNA
<213> ORGANISM: Artificial Sequence
<220> FEATURE:

<223> OTHER INFORMATION: Description of Artificial Sequence: Oligo

<400> SEQUENCE: 19
gcgaccaaaa ccttgttcac taaagc                                     26

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Oligo

<400> SEQUENCE: 20
aactcagacc caagtactcg g                                          21

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Probe

<400> SEQUENCE: 21
aatcccgaat tcgttcttat gcagaacc                                   28

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Probe

<400> SEQUENCE: 22
cgcggatccc tactgatgtt gctgattg                                   28

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 23
gtccctcaga ttcacgcttc                                            20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 24
aggccattgt ttggcagctc                                            20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 25
cccagctaag ttactactag                                            20

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Oligo

<400> SEQUENCE: 26
cctcaggttt ttcgaacttg ctttcacc                                28

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 27
ctgccaccac aggaattcat cagccgtgc                               29

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 28
ggttcgacac cagaattcta tgtgcaaaca                              30

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 29
ttggcttctc gagatgttgt tg                                      22

<210> SEQ ID NO 30
<211> LENGTH: 48
<212> TYPE: DNA
<213> ORGANISM: Artificial Sequence
<220> FEATURE:
<223> OTHER INFORMATION: Description of Artificial Sequence: Oligo

<400> SEQUENCE: 30
gagccaaaga ggcctaaatc tagagaattc cctggcgagt caagggac          48

<210> SEQ ID NO 31
<211> LENGTH: 48
<212> TYPE: DNA
<213> ORGANISM: Artificial Sequence
<220> FEATURE:
<223> OTHER INFORMATION: Description of Artificial Sequence: Oligo

<400> SEQUENCE: 31
atgtggaaga ataaaacttg acgtcgacct ggtacatgag acgaggag          48

METHODS AND MEANS FOR MODIFICATION OF PLANT CHARACTERISTICS

The present invention relates to the genetic control of flowering in plants and the cloning and expression of genes involved therein. More particularly, the present invention relates to the cloning and expression of the FY gene of *Arabidopsis thaliana*, and homologues from other species, and manipulation and use of these genes in plants.

PRIOR ART

The present inventors have previously characterised FCA as an RNA binding protein that controls *Arabidopsis* flowering time (Macknight et al., 1997).

fca-1 mutant plants flower late and share phenotypic and epistatic properties with fy, fpa, fve, fld, and ld. For this reason, these mutants have been classified together in a group referred to as the autonomous promotion pathway (Simpson et al., 1999). With the exception of fy, each gene in this class has been shown to control the accumulation of mRNA encoding FLC—a MADS box transcription factor that is a potent repressor of the floral transition (Michaels and Amasino, 1999; Sheldon et al., 2000; Sheldon et al., 1999)

FCA encodes a protein with two RNP-type RNA binding domains and binds RNA in vitro (Macknight et al., 1997). In addition it bears a WW domain, a relatively well characterised protein-protein interaction module that binds to short proline-rich motifs (reviewed in Sudol and Hunter, 2000). Change of the second signature tryptophan in the WW domain (WW-WF) has been reported to maintain the folded state of the WW domain of p53 binding protein-2, while perturbing its ability to interact with its target ligand (Koepf et al., 1999).

Species for which flowering is important to crop production are numerous, essentially all crops which are grown from seed, with important examples being the cereals, rice and maize, probably the most agronomically important in warmer climatic zones, and wheat, barley, oats and rye in more temperate climates. Important seed products are oil seed rape, sugar beet, maize, sunflower, soybean and sorghum. Many crops which are harvested for their roots are, of course, grown annually from seed and the production of seed of any kind is very dependent upon the ability of the plant to flower, to be pollinated and to set seed. In horticulture, control of the timing of flowering is important. Horticultural plants whose flowering may be controlled include lettuce, endive and vegetable brassicas including cabbage, broccoli and cauliflower, and carnations and geraniums.

*Arabidopsis thaliana* is a facultative long day plant, flowering early under long days and late under short days. Because it has a small, well-characterized genome, is relatively easily transformed and regenerated and has a rapid growing cycle, *Arabidopsis* is an ideal model plant in which to study flowering and its control.

SUMMARY OF THE INVENTION

The inventors have cloned, characterised and manipulated the FY gene of *Arabidopsis thaliana* and identified homologues in other species.

Specifically, the present inventors mutated the second signature tryptophan in the WW domain to phenylalanine (WW-WF) and wild-type and mutant transgenes expressed in the late flowering fca-1 mutant. None of the lines expressing the FCA WF mutant could complement the fca-1 mutation, demonstrating that an intact WW domain is required for the function that FCA performs in flowering time control.

The present inventors then went on to identify proteins which bound to the C-terminus of FCA (which includes the WW) and eventually to identify the FY gene.

The inventors then made mutations in the FCA gene and investigated the interaction of mutant and wildtype FY proteins with FCA.

FY also plays a role in the determination of juvenile phase length, and so may be used not only to alter flowering time, but also juvenile phase length.

ASPECTS OF THE INVENTION

Accordingly, in a first aspect the present invention provides an isolated nucleic acid molecule encoding a polypeptide with FY function.

Those skilled in the art will appreciate that "FY function" refers to the ability to influence the timing of flowering phenotypically like the FY gene of *Arabidopsis thaliana*, especially the ability to complement a fy mutation of *Arabidopsis thaliana*.

An isolated nucleic acid molecule according to the invention may encode a polypeptide comprising an FY amino acid sequence shown herein (e.g. Annex 1; SEQ ID NO: 1).

The nucleic acid molecule may comprise the coding sequence of the FY gene shown in Annex 2 (SEQ ID NO: 2).

Preferably, the nucleic acid molecule consists essentially of the coding sequence of the FY gene shown in Annex 2 (SEQ ID NO: 2).

Nucleic acid according to the present invention may have the sequence of the FY gene of Arabidopsis thaliana as indicated in Annex 2 (SEQ ID NO: 2), or may be a mutant, variant, derivative or allele or a homologue of the sequence provided.

Preferred mutants, variants, derivatives and alleles are those which encode a protein which retains a functional characteristic of the protein encoded by the wild-type gene, especially the ability to alter flowering time, or juvenile phase length.

Polynucleotides which are not 100% identical to the sequences shown herein but fall within the scope of the invention can be obtained in a number of ways.

Other FY variants (for example allelic forms) of the gene described herein may be obtained for example by probing cDNA or genomic DNA libraries made from *Arabidopsis thaliana* plants or cells.

In addition, other plant (monocot or dicot) homologues of the gene may be obtained. Such sequences may be obtained by making or obtaining cDNA libraries made from dividing cells or tissues or genomic DNA libraries from other plant species, and probing such libraries with probes comprising all or part of a nucleic acid of the invention under conditions of medium to high stringency (for example for hybridization on a solid support (filter) overnight incubation at 42° C. in a solution containing 50% formamide, 5×SSC (750 mM NaCl, 75 mM sodium citrate), 50 mM sodium phosphate (pH7.6), 5×Denhardt=s solution, 10% dextran sulphate and 20 µg/ml salmon sperm DNA, followed by washing in 0.03M sodium chloride and 0.03M sodium citrate (i.e. 0.2×SSC) at from about 50° C. to about 60° C.).

Thus the present invention provides an isolated nucleic acid which hybridizes to the nucleotide sequence shown in Annex 2, SEQ ID NO: 2, under the abovementioned hybridization and washing conditions.

Such a nucleic acid is suitable for use as a probe for detecting the FY gene, for example in Southern blots.

Alternatively, polynucleotides of the invention may be obtained by site directed mutagenesis of the sequences of shown in the figures or allelic variants thereof. This may be useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides. Further changes may be desirable to represent particular coding changes which are required to provide, for example, conservative substitutions.

Changes to a sequence, to produce a mutant, variant or derivative, may be by one or more of addition, insertion, deletion or substitution of one or more nucleotides in the nucleic acid, leading to the addition, insertion, deletion or substitution of one or more amino acids in the encoded polypeptide. Of course, changes to the nucleic acid which make no difference to the encoded amino acid sequence ("degeneratively equivalent") are included.

A mutant, allele, variant or derivative amino acid sequence in accordance with the present invention may include within a sequence shown herein a single amino acid change with respect to the sequence shown in Annex 1 (SEQ ID NO: 1), or 2, 3, 4, 5, 6, 7, 8, or 9 changes, about 10, 15, 20, 30, 40 or 50 changes, or greater than about 50, 60, 70, 80 or 90 changes. In addition to one or more changes within the amino acid sequence shown in the relevant figure, a mutant, allele, variant or derivative amino acid sequence may include additional amino acids at the C-terminus and/or N-terminus.

A sequence related to a sequence specifically disclosed herein shares homology with that sequence. Homology may be at the nucleotide sequence and/or amino acid sequence level. Preferably, the nucleic acid and/or amino acid sequence shares homology with the coding sequence or the sequence encoded by a nucleotide sequence shown herein, for instance Annex 2, preferably at least about 50%, or 60%, or 70%, or 80% homology, most preferably at least about 90%, 95%, 96%, 97%, 98% or 99% homology.

As is well-understood, homology at the amino acid level is generally in terms of amino acid similarity or identity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Similarity may be as defined and determined by the TBLASTN program, of Altschul et al. (1990) *J. Mol. Biol.* 215: 403–10, which is in standard use in the art, or, and this may be preferred, either of the standard programs BestFit and GAP, which are part of the Wisconsin Package, Version 8, September 1994, (Genetics Computer Group, 575 Science Drive, Madison, Wis., USA, Wisconsin 53711). BestFit makes an optimal alignment of the best segment of similarity between two sequences. Optimal alignments are found by inserting gaps to maximize the number of matches using the local homology algorithm of Smith and Waterman (Advances in Applied Mathematics (1981) 2, pp. 482–489). GAP uses the Needleman and Wunsch algorithm to align two complete sequences that maximizes the number of matches and minimizes the number of gaps. Generally, the default parameters are used, with a gap creation penalty=12 and gap extension penalty=4.

Homology is generally over the full-length of the relevant sequence shown herein, that is unless stated otherwise, or it may be over a contiguous sequence of about or greater than about 20, 25, 30, 33, 40, 50, 67, 133, 167, 200, 233, 267, 300, 333, 400, 450, 500, 550, 600 or more amino acids or codons, compared with the relevant amino acid sequence or nucleotide sequence as the case may be.

Nucleic acid according to the present invention may consist essentially of or consist of the relevant coding sequence. Nucleic acid according to the present invention may include a promoter or other regulatory sequence as discussed further elsewhere herein, and such regulatory sequence may be heterologous to the coding sequence, that is to say not naturally operably linked therewith.

Also provided by an aspect of the present invention is nucleic acid including or consisting essentially of a sequence of nucleotides complementary to a nucleotide sequence hybridisable with any encoding sequence provided herein. Another way of looking at this would be for nucleic acid according to this aspect to be hybridisable with a nucleotide sequence complementary to any encoding sequence provided herein. Of course, DNA is generally double-stranded and blotting techniques such as Southern hybridisation are often performed following separation of the strands without a distinction being drawn between which of the strands is hybridising. Preferably the hybridisable nucleic acid or its complement encode a product able to influence e.g., flowering time e.g. in *Arabidopsis thaliana*. Preferred conditions for hybridisation are familiar to those skilled in the art, but are generally stringent enough for there to be positive hybridisation between the sequences of interest to the exclusion of other sequences.

In the context of cloning, it may be necessary for one or more gene fragments to be ligated to generate a full-length coding sequence. Also, where a full-length encoding nucleic acid molecule has not been obtained, a smaller molecule representing part of the full molecule, may be used to obtain full-length clones. Inserts may be prepared from partial cDNA clones and used to screen cDNA libraries. The full-length clones isolated may be subcloned into expression vectors and activity assayed by transfection into suitable host cells, e.g. with a reporter plasmid.

The present invention also extends to nucleic acid comprising transcriptional control sequences for the FY gene. Such control sequences will be found 5' to the open reading frame of the gene and are obtainable by probing a genomic DNA library with a nucleic acid of the invention, selecting a clone which hybridizes under conditions of medium to high stringency, and sequencing the clone 5' to the open reading frame of the gene. Where only a small amount of sequence is present in the 5' region, this sequence may be used to reprobe the library to genome walk further upstream. Analysis of the upstream region will reveal control regions for gene expression including control regions common to many genes (i.e. TATA and CAAT boxes) and other control regions, usually located from 1 to 10,000, such as 1 to 1000 or 50 to 500 nucleotides upstream of the start of transcription.

To confirm that such regions are the control regions of the gene, they may be linked to a reported gene (such as β-galactosidase) and tested in any suitable in vitro or in vivo system. For example the construct of the control region (e.g. comprising 50 to 500 nucleotides upstream of the start of transcription) and the reporter gene may be used to produce a transgenic plant and the pattern of expression, both spatially and developmentally, may be compared with that of the FY gene. Where substantially similar patterns of expression are found, this shows that the construct comprises substantially all of the control region of the wild type gene.

Isolated nucleic acid comprising such control regions obtainable by such a method form a further aspect of the present invention.

The present invention further extends to genomic DNA exon sequences found between the introns encoding a FY gene in plant. Such exon sequences may be obtained in a manner analogous to that described above for the transcriptional control sequences, with the appropriate genome walking being conducted between the intron sequences. The locations of the exons may be determined by comparing genomic and cDNA sequences of the gene, observing where the sequences line up and diverge, and looking for consensus splice sequences which define intron/exon boundaries.

The nucleic acid molecule, which may contain for example DNA encoding a polypeptide including the amino acid sequence of FY or other polypeptide disclosed herein, may be in the form of a recombinant and preferably replicable vector, for example a plasmid, cosmid, phage or Agrobacterium binary vector. The nucleic acid may be under the control of an appropriate promoter or other regulatory elements for expression in a host cell such as a microbial, e.g. bacterial, or plant cell. In the case of genomic DNA, this may contain its own promoter or other regulatory elements and in the case of cDNA this may be under the control of an appropriate promoter or other regulatory elements for expression in the host cell.

A vector including nucleic acid according to the present invention need not include a promoter or other regulatory sequence, particularly if the vector is to be used to introduce the nucleic acid into cells for recombination into the genome.

Those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual*: 2nd edition, Sambrook et al, 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference. Specific procedures and vectors previously used with wide success upon plants are described by Bevan (Nucl. Acids Res. 12, 8711–8721 (1984)) and Guerineau and Mullineaux (1993) (Plant transformation and expression vectors. In: Plant Molecular Biology Labfax (Croy RRD ed) Oxford, BIOS Scientific Publishers, pp 121–148).

Selectable genetic markers may be used consisting of chimaeric genes that confer selectable phenotypes such as resistance to antibiotics such as kanamycin, hygromycin, phosphinotricin, chlorsulfuron, methotrexate, gentamycin, spectinomycin, imidazolinones and glyphosate.

Nucleic acid molecules and vectors according to the present invention may be provided isolated and/or purified from their natural environment, in substantially pure or homogeneous form, or free or substantially free of nucleic acid or genes of the species of interest or origin other than the sequence encoding a polypeptide with the required function. Nucleic acid according to the present invention may include cDNA, RNA, genomic DNA and may be wholly or partially synthetic. Where a DNA sequence is specified, e.g. with reference to a figure, unless context requires otherwise the RNA equivalent, with U substituted for T where it occurs, is encompassed.

When introducing a chosen gene construct into a cell, certain considerations must be taken into account, well known to those skilled in the art. The nucleic acid to be inserted should be assembled within a construct which contains effective regulatory elements which will drive transcription. There must be available a method of transporting the construct into the cell. Once the construct is within the cell membrane, integration into the endogenous chromosomal material either will or will not occur. Finally, as far as plants are concerned the target cell type must be such that cells can be regenerated into whole plants.

Plants transformed with the DNA segment containing the sequence may be produced by standard techniques which are already known for the genetic manipulation of plants. DNA can be transformed into plant cells using any suitable technology, such as a disarmed Ti-plasmid vector carried by Agrobacterium exploiting its natural gene transfer ability (EP-A-270355, EP-A-0116718, NAR 12(22) 8711–87215 1984), particle or microprojectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614) other forms of direct DNA uptake (DE 4005152, WO 9012096, U.S. Pat. No. 4,684,611), liposome mediated DNA uptake (e.g. Freeman et al. *Plant Cell Physiol*. 29: 1353 (1984)), or the vortexing method (e.g. Kindle, *PNAS U.S.A*. 87: 1228 (1990d) Physical methods for the transformation of plant cells are reviewed in Oard, 1991, *Biotech. Adv*. 9: 1–11.

Agrobacterium transformation is widely used by those skilled in the art to transform dicotyledonous species. There are various approaches used for the routine production of stable, fertile transgenic plants in almost all economically relevant monocot plants (Toriyama, et al. (1988) *Bio/Technology* 6, 1072–1074; Zhang, et al. (1988) *Plant Cell Rep*. 7, 379–384; Zhang, et al. (1988) *Theor Appl Genet* 76, 835–840; Shimamoto, et al. (1989) *Nature* 338, 274–276; Datta, et al. (1990) *Bio/Technology* 8, 736–740; Christou, et al. (1991) *Bio/Technology* 9, 957–962; Peng, et al. (1991) International Rice Research Institute, Manila, Philippines 563–574; Cao, et al. (1992) *Plant Cell Rep*. 11, 585–591; Li, et al. (1993) *Plant Cell Rep*. 12, 250–255; Rathore, et al. (1993) *Plant Molecular Biology* 21, 871–884; Fromm, et al. (1990) *Bio/Technology* 8, 833–839; Gordon-Kamm, et al. (1990) *Plant Cell* 2, 603–618; D'Halluin, et al. (1992) *Plant Cell* 4, 1495–1505; Walters, et al. (1992) *Plant Molecular Biology* 18, 189–200; Koziel, et al. (1993) *Biotechnology* 11, 194–200; Vasil, I. K. (1994) *Plant Molecular Biology* 25, 925–937; Weeks, et al. (1993) *Plant Physiology* 102, 1077–1084; Somers, et al. (1992) *Bio/Technology* 10, 1589–1594; WO92/14828). In particular, Agrobacterium mediated transformation is now emerging also as an highly efficient alternative transformation method in monocots (Hiei et al. (1994) *The Plant Journal* 6, 271–282).

The generation of fertile transgenic plants has been achieved in the cereals rice, maize, wheat, oat, and barley (reviewed in Shimamoto, K. (1994) *Current Opinion in*

*Biotechnology* 5, 158–162.; Vasil, et al. (1992) *Bio/Technology* 10, 667–674; Vain et al., 1995, *Biotechnology Advances* 13 (4): 653–671; Vasil, 1996, *Nature Biotechnology* 14 page 702).

Microprojectile bombardment, electroporation and direct DNA uptake are preferred where Agrobacterium is inefficient or ineffective. Alternatively, a combination of different techniques may be employed to enhance the efficiency of the transformation process, e.g. bombardment with Agrobacterium coated microparticles (EP-A-486234) or microprojectile bombardment to induce wounding followed by co-cultivation with Agrobacterium (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants*, Vol I, II and III, *Laboratory Procedures and Their Applications*, Academic Press, 1984, and Weissbach and Weissbach, *Methods for Plant Molecular Biology*, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

An FY gene and modified versions thereof (alleles, mutants, variants and derivatives thereof), and other nucleic acid provided herein, including species homologues, may be used to modify e.g., flowering time or juvenile phase length in a transgenic plant. Nucleic acid such as a vector as described herein may be used for the production of a transgenic plant. Such a plant may possess an altered phenotype, particularly in terms of e.g., flowering time compared with wild-type (that is to say a plant that is wild-type for FY or the relevant homologue thereof).

First, forced expression of FY (for example under the control of a strong and constitutive promoter, such as the Ca MV 35 S promoter) in a wild-type background may be used to alter the flowering time of a plant prior to flowering. Second, down-regulation of FY expression, for instance by means of an antisense FY cDNA, or by use of an FY mutant, may be used to alter flowering time of a plant.

The invention further encompasses a host cell transformed with nucleic acid or a vector according to the present invention, especially a plant or a microbial cell. Thus, a host cell, such as a plant cell, including heterologous nucleic acid according to the present invention is provided. Within the cell, the nucleic acid may be incorporated within the chromosome. There may be more than one heterologous nucleotide sequence per haploid genome.

Also according to the invention there is provided a plant cell having incorporated into its genome nucleic acid, particularly heterologous nucleic acid, as provided by the present invention, under operative control of a regulatory sequence for control of expression. The coding sequence may be operably linked to one or more regulatory sequences which may be heterologous or foreign to the gene, such as not naturally associated with the gene for its expression. The nucleic acid according to the invention may be placed under the control of an externally inducible gene promoter to place expression under the control of the user.

A suitable inducible promoter is the GST-II-27 gene promoter which has been shown to be induced by certain chemical compounds which can be applied to growing plants. The promoter is functional in both monocotyledons and dicotyledons. It can therefore be used to control gene expression in a variety of genetically modified plants, including field crops such as canola, sunflower, tobacco, sugarbeet, cotton; cereals such as wheat, barley, rice, maize, sorghum; fruit such as tomatoes, mangoes, peaches, apples, pears, strawberries, bananas, and melons; and vegetables such as carrot, lettuce, cabbage and onion. The GST-II-27 promoter is also suitable for use in a variety of tissues, including roots, leaves, stems and reproductive tissues.

A further aspect of the present invention provides a method of making such a plant cell involving introduction of nucleic acid or a suitable vector including the sequence of nucleotides into a plant cell and causing or allowing recombination between the vector and the plant cell genome to introduce the sequence of nucleotides into the genome. The invention extends to plant cells containing nucleic acid according to the invention as a result of introduction of the nucleic acid into an ancestor cell.

The term "heterologous" may be used to indicate that the gene/sequence of nucleotides in question have been introduced into said cells of the plant or an ancestor thereof, using genetic engineering, i.e. by human intervention. A transgenic plant cell, i.e. transgenic for the nucleic acid in question, may be provided. The transgene may be on an extra-genomic vector or incorporated, preferably stably, into the genome. A heterologous gene may replace an endogenous equivalent gene, i.e. one which normally performs the same or a similar function, or the inserted sequence may be additional to the endogenous gene or other sequence. An advantage of introduction of a heterologous gene is the ability to place expression of a sequence under the control of a promoter of choice, in order to be able to influence expression according to preference. Furthermore, mutants, variants and derivatives of the wild-type gene, e.g. with higher or lower activity than wild-type, may be used in place of the endogenous gene. Nucleic acid heterologous, or exogenous or foreign, to a plant cell may be non-naturally occuring in cells of that type, variety or species. Thus, nucleic acid may include a coding sequence of or derived from a particular type of plant cell or species or variety of plant, placed within the context of a plant cell of a different type or species or variety of plant. A further possibility is for a nucleic acid sequence to be placed within a cell in which it or a homologue is found naturally, but wherein the nucleic acid sequence is linked and/or adjacent to nucleic acid which does not occur naturally within the cell, or cells of that type or species or variety of plant, such as operably linked to one or more regulatory sequences, such as a promoter sequence, for control of expression. A sequence within a plant or other host cell may be identifiably heterologous, exogenous or foreign.

Plants which include a plant cell according to the invention are also provided, along with any part or propagule thereof, seed, selfed or hybrid progeny and descendants. A plant according to the present invention may be one which does not breed true in one or more properties. Plant varieties may be excluded, particularly registrable plant varieties according to Plant Breeders' Rights. It is noted that a plant need not be considered a "plant variety" simply because it contains stably within its genome a transgene, introduced into a cell of the plant or an ancestor thereof.

In addition to a plant, the present invention provides any clone of such a plant, seed, selfed or hybrid progeny and descendants, and any part of any of these, such as cuttings, seed. The invention provides any plant propagule, that is any part which may be used in reproduction or propagation, sexual or asexual, including cuttings, seed and so on. Also encompassed by the invention is a plant which is a sexually or asexually propagated off-spring, clone or descendant of such a plant, or any part or propagule of said plant, off-spring, clone or descendant.

The invention further provides a method of influencing or affecting flowering time or juvenile phase length in a plant including causing or allowing expression of a heterologous nucleic acid sequence as discussed within cells of the plant.

The invention further provides a method including expression from nucleic acid encoding an FY polypeptide, or a mutant, variant, allele or derivative of the sequence, or a homologue, according to the disclosure herein, within cells of a plant (thereby producing the encoded polypeptide), following an earlier step of introduction of the nucleic acid into a cell of the plant or an ancestor thereof. Such a method may influence or affect a characteristic of the plant, such as flowering time. This may be used in combination with any other gene, such as transgenes involved in flowering or other phenotypic trait or desirable property. For example, the method may be used in conjunction with the expression of an FCA polynucleotide, or mutant, variant, allele or derivative.

The present invention also encompasses the expression product of any of the nucleic acid sequences disclosed and methods of making the expression product by expression from encoding nucleic acid therefore under suitable conditions, which may be in suitable host cells. Following expression, the product may be isolated from the expression system and may be used as desired, for instance in formulation of a composition including at least one additional component.

The present invention also provides for the production and use of fragments of the full-length polypeptides disclosed herein, especially active portions thereof. An "active portion" of a polypeptide means a peptide which is less than said full length polypeptide, but which retains an essential biological activity. In particular, the active portion retains the ability to alter flowering time, or juvenile phase length in a plant, such as *Arabidopsis thaliana*.

A "fragment" of a polypeptide means a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids. Fragments of the polypeptides may include one or more epitopes useful for raising antibodies to a portion of any of the amino acid sequences disclosed herein. Preferred epitopes are those to which antibodies are able to bind specifically, which may be taken to be binding a polypeptide or fragment thereof of the invention with an affinity which is at least about 1000× that of other polypeptides.

Purified protein according to the present invention, or a fragment, mutant, derivative or variant thereof, e.g. produced recombinantly by expression from encoding nucleic acid therefor, may be used to raise antibodies employing techniques which are standard in the art. Antibodies and polypeptides comprising antigen-binding fragments of antibodies may be used in identifying homologues from other species as discussed further below, also in identifying complexes containing FY protein.

Methods of producing antibodies include immunising a mammal (e.g. human, mouse, rat, rabbit, horse, goat, sheep or monkey) with the protein or a fragment thereof. Antibodies may be obtained from immunised animals using any of a variety of techniques known in the art, and might be screened, preferably using binding of antibody to antigen of interest. For instance, Western blotting techniques or immunoprecipitation may be used (Armitage et al, 1992, Nature 357: 80–82). Antibodies may be polyclonal or monoclonal.

As an alternative or supplement to immunising a mammal, antibodies with appropriate binding specificity may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

Antibodies raised to a polypeptide or peptide can be used in the identification and/or isolation of homologous polypeptides, and then the encoding genes. Thus, the present invention provides a method of identifying or isolating a polypeptide with the desired function (in accordance with embodiments disclosed herein), comprising screening candidate polypeptides with a polypeptide comprising the antigen-binding domain of an antibody (for example whole antibody or a suitable fragment thereof, e.g. scfv, Fab) which is able to bind a polypeptide or fragment, variant or derivative thereof according to the present invention or preferably has binding specificity for such a polypeptide. Specific binding members such as antibodies and polypeptides comprising antigen binding domains of antibodies that bind and are preferably specific for a polypeptide or mutant, variant or derivative thereof according to the invention represent further aspects of the present invention, particularly in isolated and/or purified form, as do their use and methods which employ them.

Candidate polypeptides for screening may for instance be the products of an expression library created using nucleic acid derived from an plant of interest, or may be the product of a purification process from a natural source. A polypeptide found to bind the antibody may be isolated and then may be subject to amino acid sequencing. Any suitable technique may be used to sequence the polypeptide either wholly or partially (for instance a fragment of the polypeptide may be sequenced). Amino acid sequence information may be used in obtaining nucleic acid encoding the polypeptide, for instance by designing one or more oligonucleotides (e.g. a degenerate pool of oligonucleotides) for use as probes or primers in hybridization to candidate nucleic acid, or by searching computer sequence databases, as discussed further below.

A further aspect of the present invention provides a method of identifying and cloning FY homologues from plant species other than *Arabidopsis thaliana* which method employs a nucleotide sequence derived from that shown herein. As discussed above, sequences derived from these may themselves be used in identifying and in cloning other sequences. The nucleotide sequence information provided herein, or any part thereof, may be used in a data-base search to find homologous sequences, expression products of which can be tested for ability to influence a plant characteristic. These may have ability to alter, e.g., flowering time in a plant. Alternatively, nucleic acid libraries may be screened using techniques well known to those skilled in the art and homologous sequences thereby identified then tested.

Accordingly, the present invention also extends to nucleic acid encoding a FY homologue obtained using a nucleotide sequence derived from any of those shown herein.

The provision of sequence information for the FY gene of *Arabidopsis thaliana* enables the obtention of homologous sequences from other plant species. In particular, homologues may be easily isolated from related, commercially important species, such as all members of the *Brassicaceae*, and other dicots including tobacco, sugarbeet, peas and celery. Monocots included in this category are the cereals rice, wheat and barley.

Thus, included within the scope of the present invention are nucleic acid molecules which encode amino acid sequences which are homologues of FY of *Arabidopsis thaliana*. Homology may be at the nucleotide sequence and/or amino acid sequence level, as has already been discussed above. A homologue from a species other than *Arabidopsis thaliana* encodes a product which causes a phenotype similar to that caused by the FY gene, generally including ability to alter e.g., flowering time in a plant, such as in *Arabidopsis thaliana*. In addition, mutants, derivatives or alleles of these genes may have altered, e.g. increased or decreased, activity or ability compared with wild-type.

According to a further aspect, the present invention provides a method of identifying or a method of cloning an FY homologue, e.g. from a species other than *Arabidopsis thaliana* the method employing a nucleotide sequence derived from the sequence shown in Annex 2. Thus, a method of obtaining nucleic acid is provided, comprising hybridisation of an oligonucleotide or a nucleic acid molecule comprising such an oligonucleotide to target/candidate nucleic acid. Target or candidate nucleic acid may, for example, comprise a genomic or cDNA library obtainable from an organism known to contain or suspected of containing such nucleic acid, either monocotyledonous or dicotyledonous. Successful hybridisation may be identified and target/candidate nucleic acid isolated for further investigation and/or use.

Hybridisation may involve probing nucleic acid and identifying positive hybridisation under suitably stringent conditions (in accordance with known techniques) and/or use of oligonucleotides as primers in a method of nucleic acid amplification, such as PCR. For probing, preferred conditions are those which are stringent enough for there to be a simple pattern with a small number of hybridisations identified as positive which can be investigated further. It is well known in the art to increase stringency of hybridisation gradually until only a few positive clones remain.

For instance, screening may initially be carried out under conditions, which comprise a temperature of about 37° C. or more, a formamide concentration of less than about 50%, and a moderate to low salt (e.g. Standard Saline Citrate ("SSC")=0.15 M sodium chloride; 0.15 M sodium citrate; pH 7) concentration.

Alternatively, a temperature of about 50° C. or more and a high salt (e.g. "SSPE"=0.180 M sodium chloride; 9 mM disodium hydrogen phosphate; 9 mM sodium dihydrogen phosphate; 1 mM sodium EDTA; pH 7.4). Preferably the screening is carried out at about 37° C., a formamide concentration of about 20%, and a salt concentration of about 5×SSC, or a temperature of about 50° C. and a salt concentration of about 2×SSPE. These conditions will allow the identification of sequences which have a substantial degree of homology (similarity, identity) with the probe sequence, without requiring the perfect homology for the identification of a stable hybrid.

Suitable conditions include, e.g. for detection of sequences that are about 80–90% identical, hybridization overnight at 42°C in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_4$, pH 7.2, 6.5% SDS, 10% dextran sulfate and a final wash at 60° C. in 0.1×SSC, 0.1% SDS.

An alternative is a solution of 5×SSPE (final 0.9 M NaCl, 0.05M sodium phosphate, 0.005M ethylenediamnetetraacetic acid (EDTA) pH 7.7), 5×Denhardt=s solution, 0.5% SDS (sodium dodecyl sulphate), at 65°C overnight, (for high stringency, highly similar sequences) or 50° C. (for low stringency, less similar sequences). Washes in 0.2×SSC/0.1% SDS at 65° C. for high stringency, alternatively at 50–60° C. in 1×SSC/0.1% SDS for low stringency.

The present invention extends to nucleic acid selectively hybridisable under high stringency with nucleic acid identified herein.

As an alternative to probing, though still employing nucleic acid hybridisation, oligonucleotides designed to amplify DNA sequences may be used in PCR reactions or other methods involving amplification of nucleic acid, using routine procedures. See for instance "PCR protocols; A Guide to Methods and Applications", Eds. Innis et al, 1990, Academic Press, New York.

Preferred primers for amplification of regions of FY for use as probes to obtain genomic or cDNA clones may include the following combinations:

GSO 384+387
GSO 363+382
GSO 394+397
GSO 392+395
GSO 391+393
GSO 388+390
GSO 386+389

The sequences of the oligonucleotides are given in the Examples.

On the basis of amino acid sequence information oligonucleotide probes or primers may be designed, taking into account the degeneracy of the genetic code, and, where appropriate, codon usage of the organism from the candidate nucleic acid is derived.

Preferably an oligonucleotide in accordance with certain embodiments of the invention, e.g. for use in nucleic acid amplification, is up to about 50 nucleotides, or about 40 nucleotides or about 30 or fewer nucleotides in length (e.g. 18, 21 or 24).

Assessment of whether or not such a PCR product corresponds to a homologue gene may be conducted in various ways. A PCR band from such a reaction might contain a complex mix of products. Individual products may be cloned and each one individually screened. It may be analysed by transformation to assess function on introduction into a plant of interest.

As noted, nucleic acid according to the present invention is obtainable using oligonucleotides, designed on the basis of sequence information provided herein, as probes or primers. Nucleic acid isolated and/or purified from one or more cells of a plant (see above), or a nucleic acid library derived from nucleic acid isolated and/or purified from the plant (e.g. a cDNA library derived from mRNA isolated from the plant), may be probed under conditions for selective hybridisation and/or subjected to a specific nucleic acid amplification reaction such as the polymerase chain reaction (PCR). The nucleic acid probed or used as template in the amplification reaction may be genomic DNA, cDNA or RNA. If necessary, one or more gene fragments may be ligated to generate a full-length coding sequence.

PCR primers derived from the FY sequences disclosed herein may readily be tested for their specificity for amplifying nucleic acid according to the present invention, using both genomic DNA and RT-PCR templates. Cloning and subsequent sequencing of PCR products may be used to indicate amplification of the expected derived gene fragment. Full length cDNA clones can be obtained as described by 5' and 3' RACE technology if RT-PCR products are used as templates.

Various aspects of the present invention include the obtainable nucleic acid, methods of screening material, e.g. cell lysate, nucleic acid preparations, for the presence of nucleic acid of interest, methods of obtaining the nucleic acid, and suitable primers and primer combinations.

The sequence information provided herein also allows the design of diagnostic tests for determination of the presence of a specific gene or allele thereof in any given plant, cultivar, variety, population, landrace, part of a family or other selection in a breeding programme or other such genotype. A diagnostic test may be based on determination of the presence or absence of a particular allele by means of nucleic acid or polypeptide determination.

At the nucleic acid level, this may involve hybridisation of a suitable oligo- or poly-nucleotide, such as a fragment of the gene or a homologue thereof, including any homologue disclosed herein, or any particular allele, such as an allele which gives a desirable phenotype, such as any such allele disclosed herein. The hybridisation may involve PCR designed to amplify a product from a given allelic version of the gene, with subsequent detection of an amplified product by any of a number of possible methods including but not limited to gel electrophoresis, capillary electrophoresis, direct hybridisation of nucleotide sequence probes and so on. A diagnostic test may be based on PCR designed to amplify various alleles or any allele from the relevant locus, with a test to distinguish the different possible alleles by any of a number of possible methods, including DNA fragment size, restriction site variation (e.g. CAPS—cleaved amplified polymorphic sites) and so on. A diagnostic test may also be based on a great number of possible variants of nucleic acid analysis that will be apparent to those skilled in the art, such as use of a synthetic sequence as a hybridisation probe.

Broadly, the methods divide into those screening for the presence of nucleic acid sequences and those that rely on detecting the presence or absence of a polypeptide. The methods may make use of biological samples from one or more plants or cells that are suspected to contain the nucleic acid sequences or polypeptide.

Exemplary approaches for detecting nucleic acid or polypeptides include analysing a sample from the plant or plant cell by:

(a) comparing the sequence of nucleic acid in the sample with all or part of a nucleotide sequence shown herein, to determine whether the sample contains a mutation;

(b) determining the presence in the sample of a polypeptide including an FY amino acid sequence shown herein, or a fragment thereof and, if present, determining whether the polypeptide is full length, and/or is mutated, and/or is expressed at the normal level;

(c) performing DNA fingerprinting to compare the restriction pattern produced when a restriction enzyme cuts nucleic acid in the sample with the restriction pattern obtained from a nucleotide sequence shown herein, or from a known mutant, allele or variant thereof;

(d) contacting the sample with a specific binding member capable of binding to nucleic acid including the nucleotide sequence as set out herein, or a fragment thereof, or a mutant, allele or variant thereof, the specific binding member including nucleic acid hybridisable with a FY sequence herein, or a polypeptide including a binding domain with specificity for nucleic acid including a FY sequence or polypeptide encoded by it, or a mutated form thereof, and determining binding of the specific binding member;

(e) performing PCR involving one or more primers based on a nucleotide sequence shown herein to screen the sample for nucleic acid including the nucleotide sequence of Annex 2 or a mutant, allele or variant thereof.

When screening for a FY allele nucleic acid, the nucleic acid in the sample will initially be amplified, e.g. using PCR, to increase the amount of the analyte as compared to other sequences present in the sample. This allows the target sequences to be detected with a high degree of sensitivity if they are present in the sample. This initial step may be avoided by using highly sensitive array techniques that are becoming increasingly important in the art.

A variant form of the gene may contain one or more insertions, deletions, substitutions and/or additions of one or more nucleotides compared with the wild-type sequence which may or may not disrupt or alter the gene function. Differences at the nucleic acid level are not necessarily reflected by a difference in the amino acid sequence of the encoded polypeptide. However, a mutation or other difference in a gene may result in a frame-shift or stop codon, which could seriously affect the nature of the polypeptide produced (if any), or a point mutation or gross mutational change to the encoded polypeptide, including insertion, deletion, substitution and/or addition of one or more amino acids or regions in the polypeptide. A mutation in a promoter sequence or other regulatory region may prevent or reduce expression from the gene or affect the processing or stability of the mRNA transcript.

Tests may be carried out on preparations containing genomic DNA, cDNA and/or mRNA. Testing cDNA or mRNA has the advantage of the complexity of the nucleic acid being reduced by the absence of intron sequences, but the possible disadvantage of extra time and effort being required in making the preparations. RNA is more difficult to manipulate than DNA because of the wide-spread occurrence of RNases.

Nucleic acid in a test sample may be sequenced and the sequence compared with a sequence shown herein to determine whether or not a difference is present. If so, the difference can be compared with known alleles to determine whether the test nucleic acid contains one or more of the variations indicated, or the difference can be investigated for association with a desired phenotype.

The amplified nucleic acid may then be sequenced as above, and/or tested in any other way to determine the presence or absence of a particular feature. Nucleic acid for testing may be prepared from nucleic acid removed from cells or in a library using a variety of other techniques such as restriction enzyme digest and electrophoresis.

Nucleic acid may be screened using a variant- or allele-specific probe. Such a probe corresponds in sequence to a region of the gene, or its complement, containing a sequence alteration known to be associated with alteration of ability to affect e.g., flowering time. Under suitably stringent conditions, specific hybridisation of such a probe to test nucleic acid is indicative of the presence of the sequence alteration in the test nucleic acid. For efficient screening purposes, more than one probe may be used on the same test sample.

Allele- or variant-specific oligonucleotides may similarly be used in PCR to specifically amplify particular sequences if present in a test sample. Assessment of whether a PCR band contains a gene variant may be carried out in a number of ways familiar to those skilled in the art. The PCR product may for instance be treated in a way that enables one to display the mutation or polymorphism on a denaturing polyacrylamide DNA sequencing gel, with specific bands that are linked to the gene variants being selected.

An alternative or supplement to looking for the presence of variant sequences in a test sample is to look for the presence of the normal sequence, e.g. using a suitably specific oligonucleotide probe or primer.

Approaches which rely on hybridisation between a probe and test nucleic acid and subsequent detection of a mismatch may be employed. Under appropriate conditions (temperature, pH etc.), an oligonucleotide probe will hybridise with a sequence which is not entirely complementary. The degree of base-pairing between the two molecules will be sufficient for them to anneal despite a mis-match. Various approaches are well known in the art for detecting the presence of a mis-match between two annealing nucleic acid molecules.

For instance, RNase A cleaves at the site of a mis-match. Cleavage can be detected by electrophoresing test nucleic acid to which the relevant probe or probe has annealed and looking for smaller molecules (i.e. molecules with higher electrophoretic mobility) than the full length probe/test hybrid. Other approaches rely on the use of enzymes such as resolvases or endonucleases.

Thus, an oligonucleotide probe that has the sequence of a region of the normal gene (either sense or anti-sense strand) in which mutations associated with particular phenotypes are known to occur may be annealed to test nucleic acid and the presence or absence of a mis-match determined. Detection of the presence of a mis-match may indicate the presence in the test nucleic acid of a mutation. On the other hand, an oligonucleotide probe that has the sequence of a region of the gene including a mutation may be annealed to test nucleic acid and the presence or absence of a mis-match determined. The presence of a mis-match may indicate that the nucleic acid in the test sample has the normal sequence, or a different mutant or allele sequence. In either case, a battery of probes to different regions of the gene may be employed.

The presence of differences in sequence of nucleic acid molecules may be detected by means of restriction enzyme digestion, such as in a method of DNA fingerprinting where the restriction pattern produced when one or more restriction enzymes are used to cut a sample of nucleic acid is compared with the pattern obtained when a sample containing the normal gene or a variant or allele is digested with the same enzyme or enzymes.

The presence of absence of a lesion in a promoter or other regulatory sequence may also be assessed by determining the level of mRNA production by transcription or the level of polypeptide production by translation from the mRNA.

Nucleic acid isolated and/or purified from one or more cells of a plant or a nucleic acid library derived from nucleic acid isolated and/or purified from cells (e.g. a cDNA library derived from mRNA isolated from the cells), may be probed under conditions for selective hybridisation and/or subjected to a specific nucleic acid amplification reaction such as the polymerase chain reaction (PCR).

A method may include hybridisation of one or more (e.g. two) probes or primers to target nucleic acid. Where the nucleic acid is double-stranded DNA, hybridisation will generally be preceded by denaturation to produce single-stranded DNA. The hybridisation may be as part of a PCR procedure, or as part of a probing procedure not involving PCR. An example procedure would be a combination of PCR and low stringency hybridisation. A screening procedure, chosen from the many available to those skilled in the art, is used to identify successful hybridisation events and isolate hybridised nucleic acid.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR, RNAase cleavage and allele specific oligonucleotide probing.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. DNA for probing may be prepared from RNA preparations from cells.

Preliminary experiments may be performed by hybridising under low stringency conditions various probes to Southern blots of DNA digested with restriction enzymes. Suitable conditions would be achieved when a large number of hybridising fragments were obtained while the background hybridisation was low. Using these conditions nucleic acid libraries, e.g. cDNA libraries representative of expressed sequences, may be searched.

As noted, those skilled in the art are well able to employ suitable conditions of the desired stringency for selective hybridisation, taking into account factors such as oligonucleotide length and base composition, temperature and so on.

In some preferred embodiments of diagnostic assays according to the present invention, oligonucleotides according to the present invention that are fragments of any of the sequences shown herein, or any allele associated with a desired phenotype are at least about 10 nucleotides in length, more preferably at least about 15 nucleotides in length, more preferably at least about 20 nucleotides in length, more preferably about 30 nucleotides in length. Such fragments themselves individually represent aspects of the present invention. Fragments and other oligonucleotides may be used as primers or probes as discussed but may also be generated (e.g. by PCR) in methods concerned with determining the presence in a test sample of a sequence indicative of a desired phenotype.

There are various methods for determining the presence or absence in a test sample of a particular polypeptide, such as a polypeptide including the amino acid sequence shown in Annex 1, or an amino acid sequence mutant, variant or allele thereof.

A sample may be tested for the presence of a binding partner for a specific binding member such as an antibody (or mixture of antibodies), specific for one or more particular variants of a polypeptide shown herein.

In such cases, the sample may be tested by being contacted with a specific binding member such as an antibody under appropriate conditions for specific binding, before binding is determined, for instance using a reporter system as discussed. Where a panel of antibodies is used, different reporting labels may be employed for each antibody so that binding of each can be determined.

A specific binding member such as an antibody may be used to isolate and/or purify its binding partner polypeptide from a test sample, to allow for sequence and/or biochemical analysis of the polypeptide to determine whether it has the sequence and/or properties of the wild-type polypeptide or a particular mutant, variant or allele thereof. Amino acid sequence is routine in the art using automated sequencing machines.

The use of diagnostic tests for alleles allows the researcher or plant breeder to establish, with full confidence and independent from time consuming biochemical tests, whether or not a desired allele is present in the plant of interest (or a cell thereof), whether the plant is a representative of a collection of other genetically identical plants (e.g. an inbred variety or cultivar) or one individual in a sample of related (e.g. breeders=selection) or unrelated plants.

In a breeding scheme based on selection and selfing of desirable individuals, nucleic acid or polypeptide diagnostics for the desirable allele or alleles in high throughput, low cost assays as provided by this invention, reliable selection for the can be made at early generations and on more material than would otherwise be possible. This gain in reliability of selection plus the time saving by being able to test material earlier and without costly phenotype screening is of considerable value in plant breeding.

Nucleic acid-based determination of the presence or absence of one or more desirable alleles may be combined with determination of the genotype of the flanking linked genomic DNA and other unlinked genomic DNA using established sets of markers such as RFLPs, microsatellites or SSRs, AFLPs, RAPDs etc. This enables the researcher or plant breeder to select for not only the presence of the desirable allele but also for individual plant or families of plants which have the most desirable combinations of linked and unlinked genetic background. Such recombinations of desirable material may occur only rarely within a given segregating breeding population or backcross progeny. Direct assay of the locus as afforded by the present invention allows the researcher to make a stepwise approach to fixing (making homozygous) the desired combination of flanking markers and alleles, by first identifying individuals fixed for one flanking marker and then identifying progeny fixed on the other side of the locus all the time knowing with confidence that the desirable allele is still present.

The present disclosure provides sufficient information for a person skilled in the art to obtain genomic DNA sequence for any given new or existing allele and devise a suitable nucleic acid- and/or polypeptide-based diagnostic assay. In designing a nucleic acid assay account is taken of the distinctive variation in sequence that characterises the particular variant allele.

Nucleic acid according to the invention may include a nucleotide sequence encoding a product able to influence or affect, e.g., flowering time. Reducing or increasing the level of expression may be used to manipulate such a characteristic in a plant. This may involve use of anti-sense or sense regulation, discussed further below.

Nucleic acid according to the invention, such as a FY gene or homologue, may be placed under the control of an externally inducible gene promoter to place expression under the control of the user. An advantage of introduction of a heterologous gene into a plant cell, particularly when the cell is comprised in a plant, is the ability to place expression of the gene under the control of a promoter of choice, in order to be able to influence gene expression, and therefore e.g., flowering time, according to preference. Furthermore, mutants and derivatives of the wild-type gene, e.g. with higher or lower activity than wild-type, may be used in place of the endogenous gene.

In the present invention, over-expression may be achieved by introduction of the nucleotide sequence in a sense orientation. Thus, the present invention provides a method of influencing e.g., the flowering time of a plant, the method including causing or allowing expression of the product (polypeptide or nucleic acid transcript) encoded by heterologous nucleic acid according to the invention from that nucleic acid within cells of the plant.

Down-regulation of expression of a target gene may be achieved using anti-sense technology or "sense regulation" ("co-suppression").

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) *Nature* 334, 724–726; Zhang et al, (1992) *The Plant Cell* 4, 1575–1588, English et al., (1996) *The Plant Cell* 8, 179–188. Antisense technology is also reviewed in Bourque, (1995), *Plant Science* 105, 125–149, and Flavell, (1994) *PNAS USA* 91, 3490–3496.

An alternative is to use a copy of all or part of the target gene inserted in sense, that is the same, orientation as the target gene, to achieve reduction in expression of the target gene by co-suppression. See, for example, van der Krol et al., (1990) *The Plant Cell* 2, 291–299; Napoli et al., (1990) *The Plant Cell* 2, 279–289; Zhang et al., (1992) *The Plant Cell* 4, 1575–1588, and U.S. Pat. No. 5,231,020.

The complete sequence corresponding to the coding sequence (in reverse orientation for anti-sense) need not be used. For example fragments of sufficient length may be used. It is a routine matter for the person skilled in the art to screen fragments of various sizes and from various parts of the coding sequence to optimise the level of anti-sense inhibition. It may be advantageous to include the initiating methionine ATG codon, and perhaps one or more nucleotides upstream of the initiating codon. A further possibility is to target a conserved sequence of a gene, e.g. a sequence that is characteristic of one or more genes, such as a regulatory sequence.

The sequence employed may be about 500 nucleotides or less, possibly about 400 nucleotides, about 300 nucleotides, about 200 nucleotides, or about 100 nucleotides. It may be possible to use oligonucleotides of much shorter lengths, 14–23 nucleotides, although longer fragments, and generally even longer than about 500 nucleotides are preferable where possible, such as longer than about 600 nucleotides, than about 700 nucleotides, than about 800 nucleotides, than about 1000 nucleotides or more.

It may be preferable that there is complete sequence identity in the sequence used for down-regulation of expression of a target sequence, and the target sequence, though total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a mutant, derivative, variant or allele, by way of insertion, addition, deletion or substitution of one or more nucleotides, of such a sequence. The sequence need not include an open reading frame or specify an RNA that would be translatable. It may be preferred for there to be sufficient homology for the respective anti-sense and sense RNA molecules to hybridise. There may be down regulation of gene expression even where there is about 5%, 10%, 15% or 20% or more mismatch between the sequence used and the target gene.

Generally, the transcribed nucleic acid may represent a fragment of a gene, or the complement thereof, or may be a mutant, derivative, variant or allele thereof, in similar terms as discussed above in relation to alterations being made to a coding sequence and the homology of the altered sequence. The homology may be sufficient for the transcribed anti-sense RNA to hybridise with nucleic acid within cells of the plant, though irrespective of whether hybridisation takes place the desired effect is down-regulation of gene expression.

Thus, the present invention also provides a method of modifying, affecting, altering or modulating flowering time or juvenile phase length, the method including causing or allowing anti-sense transcription from heterologous nucleic acid according to the invention within cells of the plant.

The present invention further provides the use of the nucleotide sequence of FY, or a fragment, mutant, derivative, allele, variant or homologue thereof for down-regulation of gene expression, particularly down-regulation of expression of an FY gene or homologue thereof, preferably in order to influence e.g., flowering time.

When additional copies of the target gene are inserted in sense, that is the same, orientation as the target gene, a range of phenotypes is produced which includes individuals where over-expression occurs and some where under-expression of protein from the target gene occurs. When the inserted gene is only part of the endogenous gene the number of under-expressing individuals in the transgenic population increases. The mechanism by which sense regulation occurs, particularly down-regulation, is not well-understood. However, this technique is also well-reported in scientific and patent literature and is used routinely for gene control. See, for example, van der Krol et al., (1990) *The Plant Cell* 2, 291–229; Napoli et al., (1990) The Plant Cell 2, 279–289; Zhang et al, 1992 *The Plant Cell* 4, 1575–1588.

Again, fragments, mutants and so on may be used in similar terms as described above for use in anti-sense regulation.

Thus, the present invention also provides a method of influencing a characteristic of a plant, e.g. flowering time, the method including causing or allowing expression from nucleic acid according to the invention within cells of the plant. This may be used to suppress activity of a product with ability to influence e.g., flowering time. Here the activity of the product is preferably suppressed as a result of under-expression within the plant cells.

Aspects and embodiments of the present invention will now be illustrated, by way of example, with reference to the accompanying Annexes. Further aspects and embodiments will be apparent to those skilled in the art. All documents mentioned in this text are incorporated herein by reference.

Sequence Annexes

Annex 1 shows the deduced amino acid sequence of FY; SEQ ID NO: 1.

Annex 2 shows the nucleotide sequence of FY; SEQ ID NO: 2.

EXAMPLE 1

Identification of Proteins that Interact with the WW Domain of FCA

We set out to identify proteins that FCA might interact with through its WW domain. We screened cDNA expression libraries with recombinant FCA and an Arabidopsis yeast two-hybrid library for proteins interacting with FCA, but without success.

We then turned to a two-step affinity precipitation/far-western based strategy. The C-terminal region of FCA (including the WW domain) was expressed as a Histidine-tagged translation fusion from the plasmid pRSETc in *E. coli* BL384 cells. The recombinant protein (known as FCA#6) was purified by affinity chromatography on Ni NTA agarose.

Purified FCA protein was then coupled to N-hydroxysuccimidyl chloroformate activated agarose beads. The FCA coupled-beads were incubated with Arabidopsis extract and FCA-binding proteins were isolated by pelleting the beads by centrifugation. FCA binding proteins were then released from the beads by heat-treatment in SDS PAGE loading buffer and separated by SDS PAGE. The proteins were then transferred to PVDF membrane by electroblotting and probed for FCA interacting proteins by far-western analysis.

The recombinant FCA protein used as a probe was expressed as a translational fusion to glutathione-S-transferase and the recognition sequence for the catalytic subunit of heart muscle cAMP-dependent protein kinase (HMK). The C-terminal region of FCA was cloned into the plasmid pGTK (Stone et al., 1994) then sub-cloned into pGex 6p-1 (Pharmacia Biotech) and expressed in *E. coli* DH5alpha cells. The recombinant fusion protein was purified by affinity chromatography using glutathione sepharose and the glutathione-s-transferase tag was subsequently cleaved from the HMK target sequence tagged-FCA by treatment with precission protease. The tagged FCA protein was labelled with $[\gamma\text{-}^{32}P]$ by incubation with heart muscle kinase and $[\gamma^{32}P]ATP$ and incubated with the filter. After washing, the binding of the $[\gamma\text{-}^{32}P]FCA$ probe to proteins on the filter was revealed by exposure to a phosphoimager detection screen.

We found that FCA interacted with a protein that migrated with an apparent molecular weight of approximately 86 kda. When this affinity precipitation step was repeated with recombinant FCA mutated in the WW domain (WF, as described above) no interaction with a protein migrating at this apparent molecular weight could be detected. This suggested that the interaction depended on a functionally intact WW domain.

We next investigated whether this interaction could be detected in extracts prepared from other flowering time mutants. We found that this interaction could be detected in extracts prepared from various flowering time mutant backgrounds, such as fve-2, fpa-2, fwa-1 and ap1, but could not be detected in fy-1. As mentioned above, FY has been classified in the same genetic pathway as FCA.

This finding suggested that either FCA interacted with FY— and the 86 kDa protein was FY, or that the 86 kDa protein functioned upstream of the 86 kDa protein to somehow affect its interaction with FCA. We initiated three approaches to resolve these possibilities.

1. Proteomics Based Identification of 86 kda Ligand.

We attempted to purify sufficient quantities of the 86 kDa ligand to facilitate direct protein sequencing.

2. Map-based Cloning of fy-1

The late-flowering fy-1 mutation was identified by (Koornneef et al., 1991) and genetically mapped to 0.6 cM north of tt4 on chromosome V (Koornneef et al., 1994). We crossed the only known allele of fy, a Landsberg erecta (Ler) accession, fy-1, with the Columbia (Col) accession to prepare a mapping population. FLC is a major modifier of Arabidopsis flowering time and differs in apparent allellic strength between Ler and Col and is located north of the mapped position for fy-1 (Koornneef et al., 1994). We monitored the usefulness of mapping populations with markers able to distinguish Ler and Col FLC and the region of chromosome V to which fy-1 had been mapped. In a pilot experiment performed with 3 F2 populations (120 individuals per F2 population) each derived from independent crosses, we genotyped the latest flowering 21 of these 360 individuals. All were homozygous for the strong Col allele of FLC, and none were homozygous for Ler in the fy region. This suggested that it would be impossible to identify fy-1 in these mapping populations by conventional procedures on the basis of late-flowering phenotype alone. This is because the fy-1 phenotype is relatively weak and is effectively obscured by the modification in flowering time resulting from allelic variation at FLC. Normalization of both Col and Ler FLC identity by introgression and the use of recombinant inbred lines was initiated as a potential means of overcoming this problem, but fy-1 was identified before the utility of these populations could be examined.

3. Candidate Gene Approach

Our inability to detect the interaction of FCA with the 86 kDa ligand in extracts of fy-1 suggested that either the 86 kDa ligand was FY or that FY somehow affected this interaction. If one assumed that the 86 kDa ligand was indeed FY then one could take steps to identify candidate genes encoding the 86 kDa ligand in the sequenced Arabidopsis genome based on predicted size, chromosomal location and protein sequence.

The candidate gene should be approximately 86 kda in size, reside around 0.6 cM (120 kb) north of tt4 on chromosome V (Koornneef et al., 1994) and have proline-rich sequence motifs able to interact with the FCA WW domain. Some predictions about the type of proline-rich sequence the FCA WW domain is likely to bind can be made on the basis of recent studies into WW domain structure and function.

WW domains are protein-protein interaction modules that bind to short proline-rich motifs. Based on their ligand predilection, WW domains have been classified into four groups (Bedford et al., 2000; Sudol and Hunter, 2000). One major group (Group I) binds polypeptides with the minimal core consensus Pro-Pro-X-Tyr and the other (Group II) binds polypeptides with the minimal core consensus Pro-Pro-Leu-Pro (SEQ ID NO: 3) motifs. The Group III WW domains select polyproline motifs flanked by Arg or Lys and the Group IV is represented by WW domains with preference for phopho-Ser-Pro containing ligands.

The WW domain forms a compact three-stranded, antiparallel beta sheet. The two signature tryptophan residues of the WW domain are spaced 20–22 amino acids apart (see Sudol and Hunter, 2000) The recent determination of the structural basis of WW domain-ligand interactions has revealed some of the molecular details that govern ligand specificity; (Huang et al., 2000; Verdecia et al., 2000) As a result it is possible to make certain predictions as to the nature of ligand a given WW domain will bind. For example, it is predicted that only those WW domains that contain arginine in loop 1 will bind pSer-Pro or pThr-Pro motifs (Zarrinpar and Lim, 2000). Since the FCA WW domain lacks such a residue in this position it is unlikely to interact with pSer-Pro or pThr-Pro motifs and is therefore unlikely to be a Group IV WW domain. Secondly, Group I WW domains possess a hydrophobic pocket in loop II that binds the Tyr in Pro-Pro-Tyr-Pro (SEQ ID NO: 4) motifs (Huang et al., 2000). In some WW domains this tyrosine pocket is eliminated by substitution of a bulky aromatic residue at the position equivalent to dystrophin Ile 3074 (Bedford et al., 2000; Huang et al., 2000). This is the case for FCA: the equivalent position in FCA is occupied by tyrosine. This suggests that FCA is unlikely to bind to Pro-Pro-Tyr-Pro (SEQ ID NO: 4) motifs and is probably not a Group I WW domain. The structural basis of the interaction of Group III WW domains with polyproline motifs flanked by Arg or Lys residues has not yet been determined. However, negatively charged acidic patches that flank the hydrophobic praline-binding surface have been implicated in governing this specificity on the basis of modelling experiments (Bedford et al., 2000) However, it is not yet clear whether comparable acidic residues are conserved in FCA.

The FCA WW domain has three aromatic residues in Beta 2. Three aromatic amino acids in the second beta sheet seem to be required for a WW domain to belong to Group II (Espanel and Sudol, 1999), although not all WW domains with three aromatics belong to Group II. In addition, homology-based searches (BLAST) with the Arabidopsis FCA sequence indicate that the Pro-Pro-Leu-Pro (SEQ ID NO: 3) binding Group II WW domains of FBP11 are most closely related to FCA (Macknight et al., 1997).

In view of all this information, we considered it most likely that the FCA WW domain could be classified as a group II WW domain and was therefore likely to interact with a protein possessing a Pro-Pro-Leu-Pro (SEQ ID NO: 3) motif.

EXAMPLE 2

Identification of FY by the Candidate Gene Approach

We therefore analyzed annotated/predicted ORFs in Arabidopsis Chromosome V in each BAC extending North from tt4 via MIPS: www.pips.bichem.mpg.de/cgibin/proj/thal/clonelist!/chr5. A candidate gene was identified in this region on BAC clone T6I14$_{13}$ 10, with the MIPs code At5g13480 and as a putative protein encoded by position 9102-14021 on this BAC. The predicted molecular weight of the deduced protein is 75,6 kDa and it contains two PPLP regions. The deduced protein sequence also includes a WD-40 repeat region, a known protein interaction module.

Based on an estimation that 1cM=approx 200 kb the genetic mapping of fy-1 (Koornneef et al., 1994) indicates that FY should reside approximately 120 kb from tt4 (chalcone synthase [CHS]). The actual distance between this candidate gene and CHS is quite close to this value—200 kb.

The sequence of FY as deduced by the inventors (Annex 2) differed from the predicted sequence in having five WD repeats rather than the predicted four.

EXAMPLE 3

Identification of a Mutation in fy-1

In order to determine whether this candidate gene was FY, we PCR amplified overlapping fragments of this gene from DNA isolated from fy-1 plants. A G to A nucleotide change was identified at the position corresponding to 10183 in the annotated gene T6I14_10 (AL391710). This position corresponds to a 3' splice acceptor site and its mutation has deleterious effects on gene expression in a number of Arabidopsis mutants. Mutation can cause intron retention, exon skipping, cryptic splicing or a combination of these events (Brown, 1996). Such events could disrupt the open reading frame by the introduction of a premature termination codon. This mutation was confirmed by the use of a dCAPs marker that was designed to produce a PCR product that could only be cleaved by HindIII if this mutation were present.

We found that the PCR product amplified from fy-1 but not Ler wild-type DNA could be cleaved in this assay confirming the existence of this mutation and distinguishing it from the sequence of wild type Arabidopsis Columbia and Landsberg accessions.

The G-A change is consistent with the use of EMS as the mutagen (Koornneef et al., 1991) and the G-A mutation in the 3' acceptor site has been identified as a deleterious mutation to gene function in a number of Arabidopsis genes (Brown, 1996).

The consequence of the mutation in fy-1, is that it would result in the production of a truncated protein that lacked the PPLP sequences. Therefore, one would predict that FCA could not interact with this protein through its WW domain, consistent with the absence of a detectable interaction between FCA and extracts of fy-1 in the affinity precipitation/far western assay described above.

If the mutation induces a premature termination codon into the fy transcript, it might be subject to nonsense mediated decay (Hentze and Kulozik, 1999) and the level of FY mRNA might therefore be reduced. Consistent with this, we found that the level of FY mRNA was reduced in fy-1 mutants compared to Landsberg wild-type.

EXAMPLE 4

The Sequence of FY is Conserved in Higher Plants

Highly related sequences to Arabidopsis FY can be identified in other plant species on the basis of EST data in Genbank e.g. *Sorghum bicolor*: BG411183 and BG487457, *Glycine max*: BE020144, *Lycopersicon esculentum*: AW035163, *Solanum tuberosum*: BE471952, in addition to shorter stretches of homology to sequences in barley and moss.

EXAMPLE 5

Recombinant FCA Interacts with Recombinant FY in a WW Domain Dependent Manner

If the protein encoded by the FY gene is equivalent to the 86 kDa ligand identified by the affinity precipitation/far-western procedure, then it should interact with FCA in a WW domain dependent manner. We expressed FCA WW and mutant FCA WF proteins as GST fusions from plasmid pGex –6A1 in BL21(DE3) cells and affinity purified them on glutathione sepharose. The recombinant proteins were not eluted from these beads but used together with the beads to perform in vitro pull-down assays. We translated the FY encoding EST plasmid (Genbank BG459222) with a T3 coupled in vitro transcription and translation system in the presence of [$^{35}$S] methionine. We incubated GST FCA coupled beads with [$^{35}$S] methionine-labelled FY and U1A (a negative control) and found that GST-FCA-WW pulled down FY but not U1A and that the efficacy of this interaction was significantly impaired when GST-FCA-WF was tested.

EXAMPLE 6

Complementation of fy-1 Mutation

Experiments are performed which are designed to complement fy-1. A TAC clone, K21P8 (located close to FY by physical mapping) has been end sequenced and found to contain the FY gene.

EXAMPLE 7

Other Observations of FY

We have over-expressed the FCA cDNA (from the first in-frame Met) with the CaMV 35S promoter in transgenic Arabidopsis plants. This results in acceleration of the floral transition in a Landsberg background and several other genotypes. However, when combined with the fy-1 mutation, this early flowering is inhibited and instead these plants flower late like fy-1. This suggests that FCA requires FY in order to promote accelerated flowering.

Arabidopsis, like many other plants passes through a juvenile vegetative phase, before entering an adult vegetative phase and then subsequently makes the floral transition to the reproductive phase. In many late-flowering mutants there is a delay in the juvenile-adult vegetative phases transition compared to wild-type. The relative proportion of this delay is similar in wild-type and these mutants (Telfer et al., 1997). However in the case of fpa (Telfer et al., 1997) and fy (S. Poethig pers comm, cited in (Simpson et al., 1999) the delay in the juvenille-adult vegetative transition is more pronounced. In other words, much more of the late flowering phenotype of these genotypes can be attributed to a delay in the juvenille-adult vegetative transition, indicating that FY may play a particularly important role in this transition as well as the floral transition.

Notably, the combination of fy-1 with fpa-2 has never been recovered (Koornneef et al., 1998) and is therefore presumed to be lethal. This suggests that FY performs an essential function in fpa that may be separate from its role in flowering time control. FCA is not required for this essential function since an fca fpa double mutant is not lethal. This suggests that FY works together with FCA but also has other roles for which FCA is not required. As far as we are aware this is the only combination of any two flowering time mutants that results in a lethal phenotype.

Protocols

Expression and Purification of #6 Protein

Plasmid encoding FCA#6 protein was transformed into *E. coli* BL384 cells. 50 ml Luria Broth (LB) plus ampicillin was inoculated with a scraping of cells from a glycerol stock and cultured overnight with constant agitation at 37° C. The following morning, 40 ml of the overnight culture was added to 400 ml LB+amp and grown for 60 min. IPTG was added to a final concentration of 0.4 mM and growth was continued for an additional 90 min. Bacteria were then pelleted by centrifugation at 3500 rpm for 10 min and resuspended in 2.9 ml of A7 (0.1 MNaPO4, 150 mM NaCl plus 10 mM imadizole. The cells were disrupted by sonication 4×30 s bursts (MSE Soniprep 150) and clarified by twice centrifuging in microfuge tubes at 13000×g for 7 min at 4° C. The supernatant was then transferred to a 15 ml sterile tube and incubated with 384 μl of a 50% slurry of Ni-NTA agarose (Qiagen) previously equilibrated with buffer A7 plus 10 mM imidazole and mixed by end over rotation for 1 h 45 min at 4° C. The beads were collected by centrifugation at 240×g for 3 min and washed twice with A7 plus 10 mM imidazole. The beads were resuspended with 890 μl buffer A7 plus 10 mM imidazole and packed into a 1 ml chromatography column. The column was washed sequentially with 712 μl A7 plus 25 mM imidazole, 783 μl A7 plus 50 mM imidazole and 178 μl A7 plus 80 mM imidazole. The tagged FCA protein was eluted with 712 μl A7 plus 80-mM imidazole. Protein yields of 0.6 μg/ul were obtained, yields of less than 0.4 μg/ul were discarded. The purified protein was dialysed against 0.1M NaPO4 buffer at pH 7.6 overnight.

Coupling of FCA to Beads

700 μl of a 50% w/v solution of N-hydroxysuccimidyl chloroformate activated agarose (obtained from Sigma, Cat. No. 8635) was washed four times in a 1.5 ml microfuge tube with 0.1M NaPO4 pH7.6 and resuspended in a total final volume of 700 μl of the same buffer. 350 μl of 0.1M ethanolamine in 0.1M NaPO4 pH7.6 was then added and the beads mixed by end-over rotation for 30 min at room-temperature. 77 μl of 1M ethanolamine pH7.4 was then added to 700 μl of the purified FCA #6 protein sample (see above), mixed, and 700 μl removed and added to the activated beads. The protein was coupled to the beads by end-over rotation for 2 h at room temperature. The beads were then collected by centrifugation at 250×g for 2 min in a microfuge. The supernatant was removed and the beads were resuspended in 0.1M ethanolamine pH7.6 and transferred to a sterile 15 ml centrifuge tube (the final volume of 0.1M ethanolamine pH7.6 was 3.5 ml). The beads were mixed again by rotation for 2 h at room temperature and stored at 4° C. overnight. The beads were subsequently washed four times with TBS (Tris buffer saline—50 mM Tris pH7.5, 150 mM NaCl) and stored as a 50% suspension in TBS plus 0.01% thimerosal (obtained from Sigma, Cat. No. T-8784). Beads with FCA protein bound in the range of 0.6–1. μg protein per μl beads were used in affinity precipitation experiments.

Expression of GST, Heart Muscle Kinase Target Sequence-tagged FCA Protein

PGex 6p-1-A1 was transformed into *E. coli* DH5alpha cells. 10 ml LB+ampicillin was innoculated with a few cells scraped from a glycerol stock and grown overnight at 37° C. with rotation. The following morning, 5 ml of the overnight culture was diluted into 45 ml LB+amp and grown for 1 h. IPTG was added to a final concentration of 0.2 mM and grown for 5 h. Cells were harvested by centrifugation at 3500 rpm for 10 min. The supernatant was discarded and the cells pellets were stored frozen at −20° C. The frozen cell pellets were thawed by the addition of 1 ml PBS supplemented with 1% v/v Triton X-100 (PBST). Cells were disrupted by sonication (MSE Soniprep 150) for 4×10s bursts. Cell debris was removed by twice centrifuging for 7 min at 13,000×g in a microfuge. The supernatant was transferred to a fresh microfuge tube containing 100μl (100%) glutathione-sepharose 4B (Pharmacia Cat No 17-0756-01) that had been previously equilibrated with PBST. The beads were mixed with the cell extract for 45 min by end-over rotation at 4° C. The beads were then washed three times with PBST and then twice with cold cleavage buffer (50 mMTris 7.5, 150 mM NaCl, 1 mM EDTA, 1 mM DTT). The beads were resuspended with 290 μl cleavage buffer, transferred to a 0.5 ml microfuge tube and incubated with 10 μl precision protease (Pharamacia Biotech Cat No 17–0843–01) for 4 h at 4° C. The beads and associated cleaved GST were then removed by centrifugation and the supernatant was transferred to a fresh microfuge tube containing 50 μl of glutathione sepaharose previously equilibrated with cleavage buffer. The beads were then removed by centrifugation and the purified protein in the supernatant stored at −20° C.

$^{32}$P Labelling of FCA

1 μg purified HMK target sequence tagged-FCA protein was incubated in a final reaction volume of 15 μl with 1.5 μl 10×HMK (200 mM Tris pH7.5, 0.9M NaCl, 120 mM MgCl2, 0.5 mMDTT), 1 μl of PKA (Sigma Cat No. P-2645, 250 units reconstituted in 25 μl 40 mM DTT) and 2.5 μl (25μCi [γ$^{32}$P] ATP for 1 h at room temperature. 15 μl of Z'-KCl buffer (25 mM Hepes/KOH pH7.7, 12.5 mM MgCl2, 20% v/v glycerol, 100 mM KCl, 0.025 mM DTT, 1.6 μg/ml BSA) was added, mixed and chromatographed on a column of Sephadex G-25 (Sigma Cat No. G-25–150) with Z'KCl as running buffer. The labelled protein was collected in the void volume.

Arabidopsis Extraction and Affinity Precipitation Procedure 400 mg fresh-weight of Arabidopsis seedlings (harvested 12 days after germination) were crushed in liquid N$_2$ and transferred to a 2 ml microfuge tube. 1.2 ml lysis buffer (12.5 mM Tris pH 7.5, 150 mM NaCl, 1% SDS) was added and the microfuge tube gently hand-warmed. The tube was then incubated in a 100° C. water bath for 5 min. Cell debris was removed by centrifugation at 13000×g for 3 min and the supernatant transferred to a fresh 1.5 ml microfuge tube. The tube was then incubated in an ice/water bath for 1 h and precipitated SDS was removed by centrifugation for 7 min at 4° C. The supernatant was removed to a fresh microfuge tube, incubated on ice for 10 min and clarified once more by centrifugation. 1 ml of the supernatant was then transferred to a fresh microfuge tube containing 20 μl FCA#6 protein coupled-beads. The beads and extract were mixed by end-over rotation for 2 h at 4° C. The beads were then washed three times by centrifugation at 240×g for 2 min, removal of supernatant followed by the addition of 500 μl TBST (25 mM Tris pH 8.0, 137 mM NaCl, 2.7 mM KCl, 0.1% v/v Tween-20). After the last wash 20 μl SDS-PAGE loading buffer was added. The tube was then incubated in a 100° C. water bath for 3 min, centrifuged at 13000×g for 3 min and the supernatant loaded and separated by conventional SDS-PAGE (8% polyacrylamide in resolving gel).

FCA Far Western

After conventional SDS-PAGE, the proteins are transferred to PVDF membrane (Millipore Cat No. IPVH 20200) by conventional electroblotting procedures. The membrane was blocked in TBST plus 1.1% w/v dried milk powder (Waitrose) for 90 min. Fresh blocking buffer was then added with 0.5×10$^6$ cpm of labelled WW domain protein and incubated with gentle agitation for 6 h at 4° C. The membrane was then washed four times with cold TBST at 4° C. and the filter sealed in plastic and exposed to a phosphoimaging screen.

GST In Vitro Pull-down Assay: GST Fusion Protein Expression and Purification

Plasmids encoding GST:FCA-WW, GST:FCA-WF and GST were transformed into *E. coli* BL21 (DE3) Lys S and inoculated from glycerol stocks into 50 ml LB+carbenicillin (60 μg/ml)+chloramphenicol (170 μg/ml). The cultures were grown overnight with constant agitation at 37° C. and each treated in the same following way: The overnight culture was used to inoculate 450 ml LB+carb+chlor in a 2L flask and grown at 37° C. for 1 h. Target protein expression was induced by the addition of 500 μl 1M IPTG and the bacteria grown for a further 2 h. Bacteria were collected by centrifugation at 4000 rpm for 15 min at 4° C. Pellets were resuspended with ice cold 25 ml PBS supplemented with protease inhibitors (PI) (Complete obtained from Boehringer Mannheim—Cat No 1697498) and sonicated with 3 bursts of 20s. The suspension was then cleared by centrifugation at 13000 rpm for 10 min at 4° C. 25 ml of the soluble protein fraction prepared from the bacterial cultures was added to 100 μl 50% glutathione sepharose previously equilibrated with PBS+PI and mixed by end-over rotation for 30 min at 4° C. After binding the suspension was spun to 2000 rpm for 2 min to sediment the resin and the supernatant removed. The resin was washed three times with 10 bed volumes (1 ml) of PBS+PI. After the final wash the resin was resuspended in 100 μl PBS and stored overnight at 4° C.

In Vitro Translation

TnT T3/T7 Coupled reticulocyte lysate was used for all translations (Promega Cat No. L5010) which were performed according to the manufacturer's instructions and stored frozen prior to use.

Pulldown Assay:

10 μl bed volume of washed GST, GST-WW, GST-WF bound sepharose was blocked for 30 min at 4° C. (Blocking buffer: 7.5 mg BSA, 25 μl glycogen, 5 ml water). After blocking, the GST-coupled sepharose was washed 3 times with IP buffer. (IP buffer: 250 μl 1M TrisHCl pH 7.5, 600 μl 5M NaCl, 20 μl NP-40, 19.15 ml water. In some pull-down assays the IP buffer was supplemented with 20 mg BSA and 100 μl Triton X-100). TnT translation products were defrosted and clarified by centrifugation at 13000 rpm for 3 min at 4° C. and 15 μl was added to the blocked and washed GST fusion sepharose. The components were then mixed by end-over rotation at 4° C. for 2 h and then washed three times with IP buffer (or IP supplemented with BSA and Triton X-100). The sepharose beads were then resuspended in 20 μl SDS-PAGE loading buffer, and incubated for 5 min in a 100° C. water bath. Following centrifugation the supernatant was loaded on an SDS-PAGE gel (10% acrylamide in resolving gel). Following electrophoresis, the gels were fixed and dried and exposed to a phophoimager screen for detection of labelled proteins.

Identification of Mutation in fy-1

DNA was isolated from fy-1 and amplified by PCR with primers listed below. The PCR products were purified using the Qiaquick PCR purification kit (Qiagen Cat no. 28104) and sequenced using cycle sequencing with Big Dye terminators (PE Applied Biosystems).

The existence of the mutation was confirmed by dCAPs. Test DNA was amplified by PCR with oligos GSO 420 and 421. PCR product was cleaved with HindIII. DNA amplified from fy-1 is cut in this reaction, while DNA amplified from wild-type plants is not.

Sequencing Oligos

The following combination of oligos was used to amplify the FY gene for sequencing:

GSO 384+387
GSO 363+382
GSO 394+397
GSO 392+395
GSO 391+393
GSO 388+390
GSO 386+389

```
GSO 384:- 5' cct att agg tcg atg gta tgg      (SEQ ID NO: 5)

GSO 387   5' aca tgg cat gac acc aaa gcg      (SEQ ID NO: 6)

GSO 363   5' caa caa tgt acg ccg gcg gcg      (SEQ ID NO: 7)

GSO 382   5' tgg ggt tgg ttg cag agt gg       (SEQ ID NO: 8)

GSO 394   5' atc gct tct tgg aag tgg cc       (SEQ ID NO: 9)

GSO 397   5' tgg acg gtt gaa acc acc acg      (SEQ ID NO: 10)

GSO 392   5' ctt aac tgg tca ggc cct ggc      (SEQ ID NO: 11)

GSO 395   5' cat tgg aag cat ttg ctg ggg      (SEQ ID NO: 12)

GSO 391   5' aaa ccc gca gat tga aat ccc      (SEQ ID NO: 13)

GSO 393   5' agg tcc att tcg aac cag cc       (SEQ ID NO: 14)

GSO 388   5' cat agt act tag cgt gaa gtg g    (SEQ ID NO: 15)

GSO 390   5' caa tct gcg ggt ttt cat gcc      (SEQ ID NO: 16)

GSO 386   5' aat tgg att ctt agg cta cat agg  (SEQ ID NO: 17)

GSO 389   5' ctt tcg agg ccg tta aaa gcc      (SEQ ID NO: 18)

fy-1 dCAPs oligos

GS0420    5' gcg acc aaa acc ttg ttc act aaa gc  (SEQ ID NO: 19)

GS0421    5' aac tca gac cca agt act cgg         (SEQ ID NO: 20)
```

Northern Analysis of FY Expression

A probe was prepared by amplifying the FY EST (Genbank BG459222) with FY1F and FY1R. Northern analysis was by conventional procedures.

```
FY1F 5' aat ccc gaa ttc gtt ctt atg cag aac c   (SEQ ID NO: 21)

FY1R 5' cgc gga tcc cta ctg atg ttg ctg att g   (SEQ ID NO: 22)
```

Construction of pFCAgamma FCA cDNA (pGGS200)

This was constructed in three parts into pBluescript II SK+. The FCA gene was subcloned from cosmid CL44B23 (Macknight et al., 1997) as an EcoRI fragment into pBluescript to create p0932. The promoter of FCA was cloned from p0392 as an EcoRI SaiI fragment (corresponding to 1-1470 Z82 992). The coding region of FCA was obtained by performing RT-PCR on Arabidopsis (Ler) RNA with primers cDNAII-I and fca3' a and reamplified using cDNAII-I and fca-3' b. This was subcloned into pBluescript KSII vector and the SalIT-SpeT fragment encoding FCA from this clone was used to make pFCAgamma FCA cDNA.

The 3' polyadenylation signal was cloned as SpeI-XhoI fragment from p0932 (9168-9763 bp Z82992)

```
cDNAII-I  5' gtc cct cag att cac gct tc      (SEQ ID NO: 23)
fca3'a    5' agg cca ttg ttt ggc agc tc      (SEQ ID NO: 24)
fca3'b    5' ccc agc taa gtt act act ag      (SEQ ID NO: 25)
```

Construction of #6 Protein

FCA cDNA (pGGS 200 see above) in pBluescript II SK+ (Stratagene) was cut with SalI and EcoRV and cloned into pBluescript II KS+ cut similarly. FCA was then cut from this plasmid with BamHI and EcoRI and cloned into pRSETc (from Invitrogen) cut similarly.

Construction of pFCAWF

The W-F mutation was introduced into pGGS200 with oligo W23F by using the U.S.E. Mutagenesis kit (Pharmacia Biotech).

W23F 5' cctcaggttttcgaacttgctttcacc (SEQ ID NO. 26)

Construction of GST-FCA Fusions for Affinity Precipitation Far-western Procedure pGGS200 was amplified by PCR using primers FCA_E2 and FCA3'a and cut with EcoRI and EcoRV and cloned into pGTK (a gift from J. Walker see Stone et al., 1994) cut with SmaI and EcoRI to make plasmid pGTK-A1. FCA was sub-cloned from this vector by cutting with BamHI and XhoI and cloned into pGex-6P-1 (Pharmacia Biotech) cut similarly to create pGex6P-A1. The W-F mutation was introduced into pGex6p-A1 using oligo W23F by using the U.S.E. Mutagenesis kit (Pharmacia Biotech) to create pGex-6p-A1 w23f.

```
FCA_E2:    5' ctg cca cca cag gaa ttc atc agc cgt gc    (SEQ ID NO: 27)
FCA_ECO    5' ggt tcg aca cca gaa ttc tat gtg caa aca   (SEQ ID NO: 28)
FCA_X_3_5  5' ttg gct tct cga gat gtt gtt g             (SEQ ID NO: 29)
```

Construction of GST WW and GST WF Used in In Vitro Pull-down

GST:FCA-WW

The FCA cDNA in pBluescript II SK+ was mutated by the Kunkel procedure to introduce an EcoR1 site within the coding sequence of FCA (with oligo GSO 213) and a SalI site immediately following the stop codon (with oligo GSO 210) to create plasmid pGGS 214. The WW domain encoding sequence of FCA was cut from pGGS214 with EcoRI and SalI and cloned into the same sites in pGEX-6p-1 (Pharmcia Biotech) in order to make GST:FCA-WW.

GST:FCA-WF

The plamsid pFCA WF (see above) was cut with EcoN1 and the mutated WW domain encoding fragment was sub-cloned into pGGS 214 cut similarly to create pGGS 214WF. This plasmid was then cut with EcoRI and SalI and the mutated WW domain fragment sub-cloned into pGEX-6p-1 (Pharmacia Biotech) cut similarly.

REFERENCES

Bedford, M. T., Sarbassova, D., Xu, J., Leder, P., and Yaffe, M. B. (2000). A novel pro-Arg motif recognized by WW domains. J Biol Chem 275, 10359–10369.

Brown, J. W. S. (1996). Arabidopsis intron mutations and pre-mRNA splicing. Plant J. 10, 771–780.

Espanel, X., and Sudol, M. (1999). A single point mutation in a group I WW domain shifts its specificity to that of group II WW domains. J Biol Chem 274, 17284–17289.

Hentze, M. W., and Kulozik, A. E. (1999). A perfect message: RNA surveillance and nonsense-mediated decay. Cell 96, 307–310.

Huang, X., Poy, F., Zhang, R., Joachimiak, A., Sudol, M., and Eck, M. J. (2000). Structure of a WW domain containing fragment of dystrophin in complex with beta-dystroglycan. Nat Struct Biol 7, 634–638.

Koepf, E. K., Petrassi, H. M., Ratnaswamy, G., Huff, M. E., Sudol, M., and Kelly, J. W. (1999). Characterization of the structure and function of W -->F WW domain variants: identification of a natively unfolded protein that folds upon ligand binding. Biochemistry 38, 14338–14351.

Koornneef, M., Alonso-Blanco, C., Blankestijn-de Vries, H., Hanhart, C. J., and Peeters, A. J. M. (1998). Genetic interactions among late flowering mutants of Arabidopsis. Genetics 148, 885–892.

Koornneef, M., Blankestijn-de Vries, H., Hanhart, C., Soppe, W., and Peeters, T. (1994). The phenotype of some late-flowering mutants is enhanced by a locus on chromosome 5 that is not effective in the Landsberg erecta wild-type. Plant J. 6, 911–919.

Koornneef, M., Hanhart, C. J., and Van der Veen, J. H. (1991). A genetic and physiological, analysis of late flowering mutants in *Arabidopsis thaliana*. Mol. Gen. Genet. 229, 57–66.

Macias, M. J., Gervais, V., Civera, C., and Oschkinat, H. (2000). Structural analysis of WW domains and design of a WW prototype. Nat Struct Biol 7, 375–379.

Macknight, R., Bancroft, I., Page, T., Lister, C., Schmidt, R., Love, K., Westphal, L., Murphy, G., Sherson, S., Cobbett, C., and Dean, C. (1997). FCA, a gene controlling flowering time in Arabidopsis, encodes a protein containing RNA-binding domains. Cell 89, 737–745.

Michaels, S. D., and Amasino, R. M. (1999). *FLOWERING LOCUS C* encodes a novel MADS domain protein that acts as a repressor of flowering. Plant Cell 11, 949–956.

Sheldon, C. C., Finnegan, E. J., Rouse, D. T., Tadege, M., Bagnall, D. J., Helliwell, C. A., Peacock, W. J., and Dennis, E. S. (2000). The control of flowering by vernalization. Curr. Op. Plant Biol. 3, 418–422.

Sheldon, C. S., Burn, J., E., Perez, P. P., Metzger, J., Edwards, J. A., Peacock, W. J., and Dennis, E. S. (1999). The FLF MADS box gene: a repressor of flowering in Arabi-

```
GSO 213  5' gag cca aag agg cct aaa tct aga gaa ttc cct ggc gag tca agg gac  (SEQ ID NO: 30)
GSO 210  5' atg tgg aag aat aaa act tga cgt cga cct ggt aca tga gac gag gag  (SEQ ID NO: 31)
``` dopsis regulated by vernalization and methylation. Plant Cell 11, 445–458.

Simpson, G. G., Gendall, A. R., and Dean, C. (1999). When to switch to flowering. Annu. Rev. Cell Dev. Biol. 99, 519–550.

Sudol, M., and Hunter, T. (2000). NeW wrinkles for an old domain. Cell 103, 1001–1004.

Stone, J. M., Collinge, M. A., Smith, R. D., Horn, M. A. and Walker, J. C. (1994) Interaction of a protein phosphatase with an Arabidopsis serine-threonine receptor kinase. Science 266 793–795.

Telfer, A., Bollman, K. M., and Poethig, S. (1997). Phase change and regulation of trichome distribution in *Arabidopsis thaliana*. Development 124, 645–654.

Verdecia, M. A., Bowman, M. E., Lu, K. P., Hunter, T., and Noel, J. P. (2000). Structural basis for phosphoserine-proline recognition by group IV WW domains. Nat Struct Biol 7, 639–643.

Zarrinpar, A., and Lim, W. A. (2000). Converging on proline: the mechanism of WW domain peptide recognition. Nat Struct Biol 7, 611–613.

```
Annex 1 Deduced amino acid sequence of FY protein - SEQ ID NO: 1

MYAGGDMHRGSQMPQPPMMRQSSASSTNINPDYHHPSGPFDPNVDSFGAKRMRKHTQRRAVDYTSTVVRYIQ

ARTWQRDSRDRTTLQPTPAAAVDMLPTVAYSDNPSTSFAAKFVHASLNKNRCSINRVLWTPSGRRLITGSQS

GEFTLWNGQSFNFEMILQAHDQPIRSMVWSHNENYMVSGDDGGTLKYWQNNMNNVKANKTAHKESIRDLsfc ktdlkfcscsddttvkvwdftkcvdessltgAGHGWDVKSVDWHPTKSLLVSGGKDQLVKLWDTRSGRELCS

LHGHKNIVLSVKWNQNGNWLLTASKDQIIKHLYDTYACNLQLYDIRTMKELQSFRGHTKDLWRGIPAMKNIL

SVGALTAPFVIGLWGRHENPQIEIPNAHDNVWDLAWHPIGYLLCRPADNPRDVLMQNQGYNEQGFGRQPDNF

QPSEASPIPGAFVPGLTRNEGTIPGIGIAMPFDASSQGDHKQPLPGSMALGAPPLPPGPHPSLLGSGQQQGY

QQQQQHQGHPQQMLPMPNMPHHQLPPSSHMPLHPHHLPRPMQMPPHGHMPPPSMPMSHQMPGSMGMQGGMNP

QMSQSHFMGAPSGVFQGQPNSGGPQMYPQGRGGFNRPQMIPGYNNPFQQQQPPLPPGPPPNNNQQHQ

Annex 2 nucleotide sequence of FY - SEQ ID NO: 2 ctactgatg ttgctgattg 9121 ttgtttggtg gagggccagg aggtaaaggt ggctgctgct gctgcacgaa ataaaatata
 9181 gacaacggat tagtcaacgg attatgctat tttagctcta cattttcaac atctaatcat
 9241 accattgaac ctagctagtg agtttaaaac tagctgagaa agttgtattg tggttcaatc
 9301 gtatcaggtg ttttgcattg ttgtgtagac attttgccta tttgcacata tatacatgtg
 9361 aaacctttac gggtatacta aataacaaaa gactagtgtt taaatgggac ctgttggaaa
 9421 gggttgttgt agcctggaat catctgtgga cggttgaaac caccacgtcc ttggggatac
 9481 atttggggtc cgccactgtt tggttgtcct tgaaatactc ctgaaggagc acccataaaa
 9541 tgactttgcg acatctgagg attcatgcca ccttgcattc cctactccaa caacaagtga
 9601 ggattaatat ctctttctac acctctctaa gatatcacta agaaaataaa acaaagagga
 9661 atccaacaca tggggtaccg acaaaagcca ggcttaagtt gtggttgaat tacaagagat
 9721 ctgagggcca taccattgat ccaggcatct gatgagacat aggcattgag ggaggtggca
 9781 tgtgaccgtg aggaggcatt tgcataggcc ggggaagatg atgagggtgc aatggcatat
 9841 gagatgatgg tggtagctga tggtgaggca tattgggcat tggaagcatt tgctgggat
 9901 gaccttggtg ttgttgttgt tgctgatacc cttgctgctg gccacttcca agaagcgatg
 9961 ggtggggacc aggtggcaaa ggaggagccc ccagtgccat ggaacctgga agaggctgtt
10021 tatgatcccc ttgagaggat gcatcaaatg gcattgctat tcctattcct gggatagtcc
10081 cctcgttccg tgtcaaccca ggcacaaatg ctccagggat tggcgatgcc tcagatggtt
10141 ggaaattatc aggttggcga ccaaaacctt gttcattata gcctgataca aattacgctt
10201 atcagtacac acaaatcaca tcttcaattt gttagtaaac actaaataaa aaacactaat
10261 ttctgacaaa tgcaacttga aagtacatgc tcaaaattaa aacagtaagt gagatactaa
```

-continued

```
10321 tgaccgagta cttgggtctg agttttttaaa gcctgtagaa atctgcacct atatcagatc
10381 agctcagctt gaccagtcaa gtctgttctt ttctacaaaa aaattcagtt aatcacggtg
10441 ccatatggct ggccgagcct gaaccttaaa aagccaaggt ccatttcgaa ccagccatta
10501 taggagtata tgactgaccc tgccagggcc tgaccagtta agcctatcac aacatcctta
10561 ctactgagat ggataaggac atagtaatta tgtactaccc acaacctatc catcccaatg
10621 cctactaaaa aatcagatac taatagccca aaaacaaacc ttggttctgc ataagaacat
10681 ctcggggatt atctgcaggc ctgtttctgc accaaaactt ggttgtgtga tcattgctac
10741 cactgcagat aatagggtta aaaatcatta tctgaagcat ttagttattc aagagcacag
10801 ggaaccacaa cacatcatag aataaaactg taaggaactc atagcaccag actattgaaa
10861 ttgctacctg caaagaagat atccaatagg atgccatgca agatcccaaa cactgttatc
10921 atgagcattt gggatttcaa tctgcgggtt ttcatgcctg ggaattaaga aaagttttca
10981 taattagata cacctcaaac aaaaaccaca aaatataagg taaagtaaga tgctactaga
11041 ctactagtat gtagatgcat catgactgaa tataaaatgt agagaagaaa catgatttaa
11101 aaaacccctta taagtgatta aaacaatagc agcatgaacg aataaataaa acagcatact
11161 gctgcacaac agtacctacc ccacaatcca atgacaaatg gagccgtcag agctcccact
11221 gacaaaatat tcttcatggc agggatgcca cgccaaagct taaaaagagt taagacaact
11281 tttaattaga aatagttgca aattagaaat atcgaagaaa caaattgaaa actcgcatcc
11341 atgggataat gtctcatatg tcgacaagta aagcatgggt acaatgataa tctttcaaag
11401 gcatatactc tagagtccta gtcaatgtac agaaaagtaa tttgatgcgg ccagtttgtc
11461 tgatttcacg tgttaaaaac atgatcatta tagaatttga cagcttacat gttacatctt
11521 tcgtgtgccc acgaaaggat tgaagctcct tcatagtcct tatatcatac agctgcagat
11581 tacatgcata agtgtcatac aaatgcttcc ataatgcaag gaaaaaatct catttacaaa
11641 tcaatatccc cccccccccc cccacccaa aagaaagtga gacttacctt aattatctga
11701 tctttcgagg ccgttaaaag ccaattgcca ttttggttcc acttcacgct aagtactatg
11761 ttttttgtgac catggctgca gaagtaagaa taggccatca aattcgtcaa agctttgaac
11821 atgaaactat aataaaatta catattacat tatgtactac ttacagtgag caaagctctc
11881 tcccagatct agtatcccag agtttgacaa gttggtcttt tccacctgac aacacagatt
11941 aaagcggtta atgatcagcc atagagaagc tctgaaatat acagcggttt ctttttattg
12001 cattattcaa atagaagtct ataaaataat gtaccagaaa ctagtaggga cttgtgggg
12061 tgccagtcaa cgctcttgac atcccaacca tggcctgcct gagttcaaaa tataaagaac
12121 cctttgatta cttcgaaagt tctcaaatat tacaaatatg aagaaaactg tgaaaacatg
12181 cctccaaaag gataggaaac ttgttataag caccaatttg gaaccttttaa aactaactaa
12241 cgttacatgg catgacacca aagcgaatct caatgacacc ttttcctatg tagcctaaga
12301 atccaattct aataacgtac agcacatctc aagcggcctt ctaaattcaa attagaagag
12361 caagcaacaa agaaataaag tatctgccgc caatctgttc aaataacatt accggttaat
12421 gagctttcat ctacgcactt ggtaaaatcc cagactttaa cagtcgtatc atcagaacac
12481 gaacagaact tcaaatctgt tttacaaaaa ctgttggata cacattgttc agttttgaga
12541 gattcattta atgcaattca acatatcaaa cttttttttta ccttaaatcg cgaattgatt
12601 ccttgtgagc agttttattg gctttcacat tgttcatatt gttctgccaa tacctgatac
12661 ataagaaaca attgatcctt attgtcacag catttgaatc atagaattct gagcttctcg
```

-continued

```
12721 tttacaacat cataagttag ggactgaaag ggaaaaacaa atttacttta atgtgcctcc 12781 atcatcacca gaaaccatat aattttcatt gtggctccat accatcgacc taataggttg 12841 atcatgtgcc tgatattgac aacaaattta aacagtcaat accaggagca gcaactatag 12901 aagaatcaaa acagaagttt caacagatta gttatacaat ctgagaaacg aacctgaaga 12961 atcatttcaa aattaaaaga ttgcccattc caaagagtaa actccccact ttgggagccc 13021 gtgataagac gtcttcctga aggtgtccac taaataaaag aaacccaatc agcaatgatc 13081 ccattaagtt ggcataatag agttaaaaca aagaaagaaa gatgttgctt tcttgaatag 13141 ataaacatgg caaacagaga ataatacaaa acacacagct ggtagaggga tataccaata 13201 cacggttgat tgaacaacgg ttcttgttta gagatgcgtg aacaaacttt gcagcaaagc 13261 ttgttgaagg attatccgaa taggcaactg tgggaagcat ctgaagcatt gatataaaag 13321 ttagatcagt aaaccattca atcttattgc aaaacccaga aaagcaaaga aatctaacat 13381 caactgctgc agctggggtt ggttgcagag tggtcctatc ccttgagtct cgctgccatg 13441 ttcgagcctg aacaaaaaca tatatggagt aaacactctc tactttagt tccatataaa 13501 gtatgagttc gttgaactac atatccatat cagttccatg acataaagac aatcctatct 13561 aatggctttt gagataaaaa ggaccgaaga attcaactgg ggaaagcaga ggctatgagt 13621 atatagacca agactaaaac tttacagaaa acaagagaaa tataatcaag cagtacaaaa 13681 ggttctaaca agaaaatact gtgagcagca atgggaatac attacctgaa tatatctaac 13741 aacggtgctg gtgtaatcaa cagctcttct ctgtgtatgc tttctcattc gtttcgcccc 13801 aaaactgtct acattggctg caacatcaga cagagagaca ttaaatctca cagtcatcac 13861 taatccgata aaaggaagac gctcaaagtc tacttacggt cgaagggggcc agatgggtgg 13921 tggtagtcgg gattgatgtt agtggaagaa gctgacgact gccgcatcat cggtggttgt 13981 ggcatctgtg aacccctgtg catatcgccg ccggcgtaca t
```

What is claimed is:

1. An isolated nucleic acid encoding the amino acid sequence of SEQ ID NO: 1.

2. An isolated nucleic acid molecule comprising the complement of the nucleic acid of claim 1.

3. A recombinant vector which comprises the nucleic acid of claim 1.

4. A vector as claimed in claim 3 wherein the nucleic acid is operably linked to a promoter for transcription in a host cell, wherein the promoter is optionally an inducible promoter.

5. A vector as claimed in claim 4 which is a plant vector.

6. A vector as claimed in claim 5, wherein the promoter is the GST-II-27 gene promoter.

7. A method of transforming a host cell comprising introducing the vector of claim 4 into a host cell.

8. A transformed host cell comprising the nucleic acid of claim 1.

9. A host cell as claimed in claim 8 which is a plant cell, optionally present in a plant.

10. A method for producing a transgenic plant, which method comprises the steps of:

(a) performing a method as claimed in claim 7 to transform a plant host cell and, (b) regenerating a plant from the transformed plant cell.

11. A transgenic plant comprising the nucleic acid of claim 1 wherein said plant has an altered flowering time or juvenile phase length.

12. A plant as claimed claim 11 which is selected from the group consisting of: rice, maize, wheat, barley, oats, rye, rape, sugar beet, sunflower, soybean, sorghum, lettuce, endive, cabbage, broccoli, cauliflower, carnation and geranium.

13. A part a propagule from a plant as claimed in claim 12, which part or propagule comprises said nucleic acid.

14. A method for accelerating flowering time or decreasing juvenile phase length in a plant, comprising introducing the nucleic acid of claim 1 into a plant, wherein said nucleic acid is expressed.

15. The method of claim 14, wherein the expression of said nucleic acid is increased.

16. The method of claim 14, further comprising the expression of the Arabidopsis FCA polynucleotide.

* * * * *